US006338855B1

(12) United States Patent
Albacarys et al.

(10) Patent No.: US 6,338,855 B1
(45) Date of Patent: Jan. 15, 2002

(54) CLEANSING ARTICLES FOR SKIN AND/OR HAIR WHICH ALSO DEPOSIT SKIN CARE ACTIVES

(75) Inventors: Lourdes Dessus Albacarys, West Chester; David Michael McAtee, Mason; George Endel Deckner, Cincinnati, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/296,334

(22) Filed: Apr. 22, 1999

Related U.S. Application Data

(63) Continuation-in-part of application No. 09/065,991, filed on Apr. 24, 1998, now abandoned, and application No. 08/974,033, filed on Nov. 19, 1997, now abandoned, which is a continuation-in-part of application No. 08/738,145, filed on Oct. 25, 1996, now abandoned, which is a continuation of application No. 08/738,668, filed on Oct. 25, 1996, now abandoned.
(60) Provisional application No. 60/083,015, filed on Apr. 24, 1998.

(51) Int. Cl.⁷ .......................... A01N 25/34; A01N 25/08

(52) U.S. Cl. ...................................... 424/409; 424/402

(58) Field of Search .................................. 424/402, 409

(56) References Cited

U.S. PATENT DOCUMENTS

| | | | |
|---|---|---|---|
| 2,877,115 A | 3/1959 | Wemyss, Jr. et al. ....... | 162/179 |
| 2,944,931 A | 7/1960 | Yang ............................ | 162/179 |
| 3,305,392 A | 2/1967 | Britt ............................ | 117/154 |
| 3,451,758 A | 6/1969 | McClain ...................... | 401/201 |
| 3,580,853 A | 5/1971 | Parran ......................... | 252/152 |
| 3,632,396 A | 1/1972 | Perez-Zamora ........... | 117/76 P |
| 3,686,025 A | 8/1972 | Morton .................... | 117/140 R |
| 3,795,624 A | 3/1974 | Feinstone ................... | 252/91 |
| 3,895,128 A | 7/1975 | Gaiser .......................... | 428/43 |
| 3,896,807 A | 7/1975 | Buchalter .................... | 128/261 |
| 3,944,694 A | 3/1976 | McQueary .................. | 428/131 |
| 3,949,137 A | 4/1976 | Akrongold et al. ......... | 428/311 |
| 3,956,551 A | 5/1976 | Richards ...................... | 428/88 |
| 4,145,302 A | 3/1979 | Doan ........................... | 252/91 |
| 4,206,195 A | 6/1980 | Bolich, Jr. et al. ............ | 424/16 |
| 4,206,196 A | 6/1980 | Davis ........................... | 424/16 |
| 4,559,157 A | 12/1985 | Smith et al. .................. | 252/90 |
| 4,574,052 A | 3/1986 | Gupte et al. .................. | 252/90 |
| 4,690,821 A | 9/1987 | Smith et al. ................ | 424/401 |
| 4,725,657 A | 2/1988 | Shibanai ..................... | 523/210 |
| 4,788,060 A | 11/1988 | Endicott et al. ............. | 424/443 |

(List continued on next page.)

FOREIGN PATENT DOCUMENTS

| | | |
|---|---|---|
| CN | 1050066 A | 3/1991 |
| CN | 1102211 A | 5/1995 |
| CN | 1106704 A | 8/1995 |
| CN | 1135320 A | 11/1996 |
| EP | 0186208 A | 7/1986 |
| EP | WO 87/02379 | 4/1987 |
| EP | 0327326 A1 | 8/1989 |
| EP | 0353013 A2 | 1/1990 |
| EP | 0485212 A1 | 5/1992 |
| EP | 0613675 A1 | 9/1994 |
| EP | 0615720 A1 | 9/1994 |
| EP | 0619074 A1 | 10/1994 |
| EP | 0550067 B1 | 9/1996 |
| GB | 1577926 | 10/1980 |
| GB | 2163947 A | 3/1986 |
| GB | 2218430 A | 11/1989 |
| GB | 2297490 A | 8/1996 |
| JP | 58-112542 | 7/1983 |
| JP | 63-097699 | 4/1988 |
| JP | 01-246478 | 10/1989 |
| JP | 6-282290 | 6/1996 |
| JP | 09-151400 | 6/1997 |
| JP | 09-216809 | 8/1997 |
| WO | WO 89/03639 | 5/1989 |
| WO | WO 93/05141 | 3/1993 |
| WO | WO 93/21899 | 11/1993 |
| WO | WO 93/25077 | 12/1993 |
| WO | WO 94/27569 | 12/1994 |
| WO | WO 95/00116 | 1/1995 |
| WO | WO 95/16824 | 6/1995 |
| WO | WO 95/31189 | 11/1995 |
| WO | WO 96/04937 | 2/1996 |
| WO | WO 96/06595 | 3/1996 |
| WO | WO 96/14835 | 5/1996 |
| WO | WO 96/24329 | 8/1996 |
| WO | WO 96/24723 | 8/1996 |
| WO | WO 96/34035 | 10/1996 |
| WO | WO 96/36315 | 11/1996 |
| WO | WO 97/07781 | 3/1997 |
| WO | WO 97/16066 | 5/1997 |
| WO | WO 97/45256 | 12/1997 |

OTHER PUBLICATIONS

Buf–Puf Singles Skin Conditioning, labeling, copyright 1991.
Buf–Puf Singles Oil–Free, labeling, copyright 1991.
Buf–Puf Singles With Cleanser for Normal to Dry Skin, labeling, copyright 1996.
Buf–Puf Singles With Cleanser for Normal to Oily Skin, labeling, copyright 1995.
Tender Bath, Westgate Laboratories, Edison, NJ,1987. (Product Description—product believed to have been test marketed in Sep., 1986).

*Primary Examiner*—Theodore J. Criares
(74) *Attorney, Agent, or Firm*—George W. Allen; Armina E. Matthews; Fumiko Tsuneki

(57) ABSTRACT

The present invention relates to a substantially dry, disposable, personal cleansing article useful for both cleansing the skin or hair and delivering skin care actives onto the skin or hair. These articles are used by the consumer by (i) wetting the dry article with water and (ii) generating lather by subjecting the wetted article to mechanical forces, e.g., rubbing. The article comprises a water insoluble substrate, a lathering surfactant, and a skin care active component. Preferably, the articles of the present invention further comprise a deposition aid and/or a conditioning component.

29 Claims, No Drawings

U.S. PATENT DOCUMENTS

| | | | |
|---|---|---|---|
| 4,803,195 A | 2/1989 | Holzner | 512/4 |
| 4,806,572 A | 2/1989 | Kellett | 521/112 |
| 4,856,541 A | 8/1989 | Kellett et al. | 132/110 |
| 4,882,221 A | 11/1989 | Bogart et al. | 428/308.8 |
| 4,891,227 A | 1/1990 | Thaman et al. | 424/443 |
| 4,891,228 A | 1/1990 | Thaman et al. | 424/443 |
| 4,904,524 A | 2/1990 | Yoh | 428/311.3 |
| 4,946,617 A | 8/1990 | Sheridan et al. | 252/91 |
| 4,948,585 A | 8/1990 | Schlein | 424/404 |
| 5,017,365 A | 5/1991 | Niedbala | 424/59 |
| 5,063,062 A | 11/1991 | Greenspan et al. | 424/443 |
| 5,112,612 A | 5/1992 | Garvey et al. | 424/400 |
| 5,139,687 A | 8/1992 | Borgher, Sr. et al. | 252/8.6 |
| 5,185,155 A | 2/1993 | Behan et al. | 424/451 |
| 5,232,613 A | 8/1993 | Bacon et al. | 252/8.6 |
| 5,236,615 A | 8/1993 | Trinh et al. | 252/174.11 |
| 5,246,611 A | 9/1993 | Trinh | 252/8.6 |
| 5,292,533 A | 3/1994 | McMahon et al. | 242/408 |
| 5,348,667 A | 9/1994 | Bacon et al. | 252/8.6 |
| 5,376,287 A | 12/1994 | Borcher, Sr. et al. | 252/8.8 |
| 5,466,460 A | 11/1995 | McMahon et al. | 424/408 |
| 5,538,732 A | 7/1996 | Smith et al. | 424/402 |
| 5,552,378 A | 9/1996 | Trinh et al. | 512/3 |
| 5,605,749 A | 2/1997 | Pike et al. | 442/60 |
| 5,661,170 A | 8/1997 | Chodosh | 514/390 |
| 5,683,971 A | 11/1997 | Rose et al. | 510/130 |
| 5,702,992 A | 12/1997 | Martin et al. | 442/123 |

CLEANSING ARTICLES FOR SKIN AND/OR HAIR WHICH ALSO DEPOSIT SKIN CARE ACTIVES

CROSS-REFERENCE TO RELATED APPLICATIONS

This application claims the benefit under 35 USC § 119(e) of the filing date of the U.S. provisional application (P&G Case 7108P) having Ser. No. 60/083,015, filed Apr. 24, 1998 in the names of Lourdes D. Albacarys, David M. McAtee, and George E. Deckner. This application is also a continuation-in-part of the copending U.S. application (P&G Case 6335R) having Ser. No. 09/065,991, filed Apr. 24, 1998 in the names of Timothy J. Fowler, Lourdes D. Albacarys, and David M. McAtee, now abandoned, which is in turn a continuation-in-part of a) the abandoned U.S. application (P&G Case 6335) having Ser. No. 08/738,145, filed Oct. 25, 1996, in the name of Timothy J. Fowler, and b) the abandoned U.S. application (P&G Case 6334C) having U.S. Ser. No. 08/974,033, filed Nov. 19, 1997 in the name of Timothy J. Fowler, which is, in turn, a file wrapper continuation of the abandoned U.S. application (P&G Case 6334) having Ser. No. 08/738,668, filed Oct. 25, 1996, in the name of Timothy J. Fowler.

TECHNICAL FIELD

The present invention relates to a substantially dry, disposable, personal cleansing article useful for both cleansing the skin or hair and delivering skin care actives to the skin or hair. These articles are used by the consumer by wetting the dry article with water, producing lather from the article, and contacting the skin with the lathered article in the normal use of cleansing the skin. These articles comprise a water insoluble substrate, at least one lathering surfactant, and at least one skin care active.

Use of the substrate enhances lathering at low surfactant levels, increases cleansing and exfoliation, optimizes delivery and deposition of the skin care active ingredients, and provides desirable characteristics such as texture, thickness and bulk. As a result, this invention provides effective cleansing using low, and hence less irritating, levels of surfactant while providing superior delivery of skin care actives to the skin or hair.

The invention also encompasses articles comprising various skin conditioning agents for delivery to the skin or hair.

The invention also encompasses a method for consistent deposition of skin care actives to the skin or hair.

The invention also encompasses a method for simultaneously cleansing the skin or hair and delivering skin care actives onto the skin or hair using the articles of the present invention and also to methods for manufacturing these articles.

BACKGROUND OF THE INVENTION

Personal cleansing articles have traditionally been marketed in a variety of forms such as bar soaps, creams, lotions, and gels. These cleansing formulations have attempted to satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and not leave the skin or hair overly dry after frequent use.

However, these traditional forms of personal cleansing articles have the inherent problem of balancing cleansing efficacy against delivering a skin care benefit. One solution to this problem is to use separate cleansing and skin care articles. However, this is not always convenient or practical and many consumers would prefer to use a single article which can both cleanse and deliver skin care benefits. In a typical cleansing composition the skin care ingredients are difficult to formulate because many skin care actives are incompatible with the surfactants, resulting in an undesirable non-homogenous mixture. To obtain a homogeneous mixture with skin care ingredients, and to prevent the loss of skin care ingredients before deposition, additional ingredients, e.g. emulsifiers, thickeners, and gellants are often added to suspend the skin care ingredients within the surfactant mixture. This results in an aesthetically pleasing homogenous mixture, but often results in poor deposition of skin care ingredients, because the skin care ingredients are emulsified and not efficiently released during cleansing. Also, many skin care agents have the disadvantage of suppressing lather generation. Lather suppression is a problem because many consumers seek cleansing articles that provide a rich, creamy, and generous lather.

Therefore, it is seen that conventional cleansing articles which attempt to combine surfactants and skin care ingredients suffer from disadvantages inherently resulting from the incompatibilities of surfactants and skin care ingredients. A need clearly exists to develop cleansing systems which provide effective cleansing and yet consistently provide sufficient skin care benefits in a single article.

It is also highly desirable to deliver cleansing and skin care benefits from a disposable, single use article. Disposable articles are convenient because they obviate the need to carry cumbersome bottles, bars, jars, tubes, and other forms of personal care products. Disposable articles are also a more sanitary alternative to the use of a sponge, washcloth, or other cleansing implement intended for multiple reuse, because such implements develop bacterial growth, unpleasant odors, and other undesirable characteristics related to repeated use.

It has been surprisingly found in the present invention that articles can be developed to provide effective cleansing and consistent delivery of skin care actives in a convenient, inexpensive, and sanitary disposable personal cleansing article having the desirable properties of a washcloth. The present invention provides the convenience of not needing to use both a separate cleansing and skin benefit article. The present invention is highly convenient to use because it is in the form of a substantially dry article that is wetted before use.

The present invention relates to a dry, disposable, personal cleansing article useful for both cleansing the skin or hair and delivering skin care actives to the skin or hair. These articles are used by the consumer by wetting the dry article with water. The articles of the present invention consist of a water insoluble substrate, at least one lathering surfactant, and at least one skin care active. In some embodiments, these articles further contain a deposition aid. Without being limited by theory, it is believed that the substrate enhances lathering at low surfactant levels, increases cleansing and exfoliation, and optimizes delivery and consistent deposition of the skin care ingredients. As a result, this invention provides effective cleansing using low, and hence less irritating, levels of surfactant while providing superior skin care benefits in a consistent and efficient manner. It has also been found that these articles are useful for delivering a wide range of conditioning ingredients to the skin or hair during the cleansing process.

Accordingly, it is an object of the present invention to provide substantially dry washcloth-like articles for both cleansing the skin or hair and delivering a skin care active to the skin or hair, wherein the articles are used in combination with water.

It is another object of the present invention to provide articles which are disposable and intended for single use.

It is another object of the present invention to provide articles which are mild to the skin or hair.

It is another object of the present invention to provide articles useful for delivering conditioning agents to the skin or hair during the cleansing process.

It is another object of the present invention to provide articles which consistently deposit skin care actives and other conditioning agents onto the skin or hair.

It is another object of the present invention to provide methods of cleansing the skin or hair and consistently delivering skin care actives onto the skin or hair.

It is another object of the present invention to provide methods of manufacturing the articles of the present invention.

These and other objects of this invention will become apparent in light of the following disclosure.

SUMMARY OF THE INVENTION

The present invention relates to disposable, single use personal care cleansing and conditioning articles comprising (A) a water insoluble substrate, (B) at least one lathering surfactant added onto or impregnated into said substrate, and (C) a skin care component comprising at least one skin care active selected from the group consisting of water soluble skin care actives, oil soluble skin care actives and mixtures thereof. The skin care active component is also added onto or impregnated into said substrate. These articles are substantially dry before wetting. Upon wetting, however, these articles are capable of generating an Average Lather Volume of greater than or equal to about 30 ml.

In further embodiments, the articles of the present invention further comprise at least one deposition aid added onto or impregnated into said substrate.

In still further embodiments, the present invention relates to methods of manufacturing these disposable, single use personal care cleansing articles. The method comprises the steps of (A) separately or simultaneously adding onto or impregnating into a water insoluble substrate (i) a lathering surfactant, and (ii) a skin care active component; and (B) substantially drying the treated substrate. The resulting article generates an Average Lather Volume of greater than or equal to about 30 ml.

In still further embodiments, the present invention relates to methods for simultaneously cleansing the skin or hair and delivering skin care actives onto the skin or hair with the personal cleansing articles described herein.

In even further embodiments, the present invention relates to methods of consistently depositing skin care active onto the skin or hair.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

DETAILED DESCRIPTION OF THE INVENTION

The personal cleansing articles of the present invention are highly efficacious for cleansing the skin or hair while at the same time providing effective deposition of skin care actives onto the skin or hair. The articles can also contain conditioning agents to be deposited onto the skin or hair.

Without being limited by theory it is believed that the substrate significantly contributes to generation of lather and deposition of skin care actives and any other conditioning agents onto the skin or hair. It is believed that this increase in lather and deposition is the result of the surface interaction of the substrate with the skin or hair. As a result, milder and significantly lower amounts of surfactants may be employed. The decreased amount of required surfactant is believed to relate to a decrease in the drying effect of the skin or hair by the surfactants. Furthermore, the diminished amount of surfactant dramatically decreases the surfactant inhibitory action (e.g., via emulsification or direct removal by the surfactants) on the deposition of skin care active ingredients onto the skin or hair.

Without being limited by theory, the substrate also enhances deposition of skin care active ingredients and conditioning agents. Since the invention is in dry form, the invention does not require emulsifiers, which can inhibit deposition of skin care active ingredients and conditioning agents. Furthermore, because the skin care active ingredients and skin conditioners are dried onto or impregnated into the substrate, they are transferred directly to the skin or hair by surface contact of the wetted article to the skin.

The substrate also enhances cleansing. The substrate can have differing textures on each side, e.g. a rough side and a smooth side. The substrate acts as an efficient lathering and exfoliating implement. By physically coming into contact with the skin or hair, the substrate significantly aids in cleansing and removal of dirt, makeup, dead skin, and other debris.

By a "lathering surfactant" is meant a surfactant, which when combined with water and mechanically agitated generates a foam or lather. Preferably, these surfactants should be mild, which means that these surfactants provide sufficient cleansing or detersive benefits but do not overly dry the skin or hair (e.g., removing too much natural oil and/or moisture), and yet meet the lathering criteria described above.

The terms "disposable" or "single use", are used herein in their ordinary sense to mean a article that is disposed or discarded after one usage event.

The terms "lathering article" or "lathered article," as used herein, means that the articles of the present invention contain enough of the surfactants described herein to generate $\geq 30$ ml of Lather Volume, as described herein in the Lather Volume Test. These Lather Volume measurements are conducted with a medium hardness water (8–10 grains per gallon) at 95° C.

The term "water-activated," as used herein, means that the present invention is presented to the consumer in dry form to be used after it is wetted with water. It is found that these articles produce a lather or are "activated" by contacting them with water and then further subjecting the article to mechanical forces, such as rubbing.

The term "substantially dry," as used herein, means that prior to use the article is substantially free of water and generally feels dry to the touch. Thus, the articles of the present invention will generally comprise less than about 10% by weight of water, preferably less than about 5% by weight of water, and more preferably less than about 1% by weight of water, the forgoing measured in a dry environment, e.g., low humidity. One of ordinary skill in the art would recognize that the water content of a article such as in the present invention can vary with the relative humidity of the environment.

The term "mild" as used herein in reference to the lathering surfactants and articles of the present invention means that the articles of the present invention demonstrate skin mildness comparable to a mild alkyl glyceryl ether sulfonate (AGS) surfactant based synthetic bar, i.e. synbar. Methods for measuring mildness, or inversely the irritancy, of surfactant containing articles, are based on a skin barrier destruction test. In this test, the milder the surfactant, the lesser the skin barrier is destroyed. Skin barrier destruction is measured by the relative amount of radio-labeled (tritium labeled) water ($3H-H_2O$) which passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, to Small et al., issued Jun. 16, 1987, which are both incorporated by reference herein in their entirety. Other testing methodologies for determining surfactant mildness well known to one skilled in the art can also be used.

The term "deposition consistency," as used herein, means that deposition of the skin care actives will be relatively unvarying no matter how the consumer prepares to use, and actually uses, the cleansing article (e.g., lathering the side of the substrate carrying the skin care actives versus lathering the substrate side with the surfactant). The articles of the present invention will have a deposition consistency of greater than about 60%, preferably greater than about 65%, more preferably greater than about 70%, and most preferably greater than about 75%. The deposition consistency measurement is the quotient obtained by dividing the amount of deposition of skin care actives that occurs via "non-ideal lathering and use" by the amount of deposition of skin care actives that occurs via "ideal lathering and use." Non-ideal lathering, as used herein, means that lathering is achieved by rubbing together or against itself the surface of the article containing the skin care actives and then contacting the skin or hair with the same surface. This causes inefficient deposition of the skin care actives because some of the skin care actives become emulsified by the surfactant. Ideal lathering, as used herein, means that lathering is achieved by rubbing together or against itself the surface of the article containing surfactant but not containing skin care actives, and then contacting the skin or hair with the surface containing the skin care actives. The same reference points would apply if both surfaces of the substrate are treated with the skin care actives (e.g. deposition obtained from lathering and contacting the skin with the same lathered surface containing emulsified skin care actives versus contacting the skin with the non-lathered surface which contains non-emulsified skin care actives). Deposition consistency is maximized when the hardness value of the skin care active component is greater than about 0.02 kg.

The personal care articles of the present invention comprise the following essential components: (A) a water insoluble substrate, (B) at least one lathering surfactant added onto or impregnated into the substrate, and (C) at least one skin care active. The articles of the present invention can further comprise of at least one deposition aid.

WATER INSOLUBLE SUBSTRATE

The articles of the present invention comprise a water insoluble substrate. By "water insoluble" is meant that the substrate does not dissolve in or readily break apart upon immersion in water. The water insoluble substrate is the implement or vehicle for delivering the lathering surfactant and the skin care actives of the present invention to the skin and/or hair. Without being limited by theory, it is believed that the substrate, as the means for transmitting mechanical forces and providing agitation, provides a lather generating effect and also aids in the deposition of the skin care actives onto the skin and/or hair.

A wide variety of materials can be used as the substrate. The following nonlimiting characteristics are desirable: (i) sufficient wet strength for use, (ii) sufficient abrasivity, (iii) sufficient loft and porosity, (iv) sufficient thickness, and (v) appropriate size.

Nonlimiting examples of suitable insoluble substrates which meet the above criteria include nonwoven substrates, woven substrates, hydroentangled substrates, air entangled substrates, natural sponges, synthetic sponges, polymeric netted meshes, and the like. Preferred embodiments employ nonwoven substrates since they are economical and readily available in a variety of materials. By nonwoven is meant that the layer is comprised of fibers which are not woven into a fabric but rather are formed into a sheet, mat, or pad layer. The fibers can either be random (i.e., randomly aligned) or they can be carded (i.e. combed to be oriented in primarily one direction). Furthermore, the nonwoven substrate can be composed of a combination of layers of random and carded fibers.

Nonwoven substrates may be comprised of a variety of materials both natural and synthetic. By natural is meant that the materials are derived from plants, animals, insects or byproducts of plants, animals, and insects. By synthetic is meant that the materials are obtained primarily from various man-made materials or from natural materials which have been further altered. The conventional base starting material is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyurethane foam, and mixtures thereof. Examples of some of these synthetic materials include acrylics such as acrilan, creslan, and the acrylonitrile-based fiber, orlon; cellulose ester fibers such as cellulose acetate, arnel, and acele; polyamides such as nylons (e.g., nylon 6, nylon 66, nylon 610, and the like); polyesters such as fortrel, kodel, and the polyethylene terephthalate fiber, dacron; polyolefins such as polypropylene, polyethylene; polyvinyl acetate fibers; polyurethane foams and mixtures thereof. These and other suitable fibers and the nonwoven materials prepared therefrom are generally described in Riedel, "Nonwoven Bonding Methods and Materials," *Nonwoven World* (1987); *The Encyclopedia Americana*, vol. 11, pp. 147–153, and vol. 26, pp. 566–581 (1984); U.S. Pat. No. 4,891,227, to Thaman et al., issued Jan. 2, 1999 and U.S. Pat. No. 4,891,228 which are all incorporated by reference herein in their entirety.

Nonwoven substrates made from natural materials consist of webs or sheets most commonly formed on a fine wire screen from a liquid suspension of the fibers. See C. A. Hampel et al., *The Encyclopedia of Chemistry*, third edition, 1973, pp. 793–795 (1973); *The Encyclopedia Americana*, vol. 21, pp. 376–383 (1984); and G. A. Smook, *Handbook of Pulp and Paper Technologies*, Technical Association for the Pulp and Paper Industry (1986); which are incorporated by reference herein in their entirety.

Substrates made from natural materials useful in the present invention can be obtained from a wide variety of commercial sources. Nonlimiting examples of suitable commercially available paper layers useful herein include Airtex®, an embossed airlaid cellulosic layer having a base weight of about 71 gsy, available from James River, Green Bay, Wis.; and Walkisoft®, an embossed airlaid cellulosic having a base weight of about 75 gsy, available from Walkisoft U.S.A., Mount Holly, N.C.

Methods of making nonwoven substrates are well known in the art. Generally, these nonwoven substrates can be made by air-laying, water-laying, meltblowing, coforning, spinbonding, or carding processes in which the fibers or filaments are first cut to desired lengths from long strands, passed into a water or air stream, and then deposited onto a screen through which the fiber-laden air or water is passed. The resulting layer, regardless of its method of production or composition, is then subjected to at least one of several types of bonding operations to anchor the individual fibers together to form a self-sustaining web. In the present invention the nonwoven layer can be prepared by a variety of processes including hydroentanglement, thermally bonding or thermo-bonding, and combinations of these processes. Moreover, the substrates of the present invention can consist of a single layer or multiple layers. In addition, a multilayered substrate can include films and other nonfibrous materials.

Nonwoven substrates made from synthetic materials useful in the present invention can also be obtained from a wide variety of commercial sources. Nonlimiting examples of suitable nonwoven layer materials useful herein include HEF 40-047, an apertured hydroentangled material containing about 50% rayon and 50% polyester, and having a basis weight of about 43 grams per square yard (gsy), available from Veratec, Inc., Walpole, Mass.; HEF 140-102, an apertured hydroentangled material containing about 50% rayon and 50% polyester, and having a basis weight of about 56 gsy, available from Veratec, Inc., Walpole, Mass.; Novonet® 149–616, a thermo-bonded grid patterned material containing about 100% polypropylene, and having a basis weight of about 50 gsy, available from Veratec, Inc., Walpole, Mass.; Novonet® 149–801, a thermo-bonded grid patterned material containing about 69% rayon, about 25% polypropylene, and about 6% cotton, and having a basis weight of about 75 gsy, available from Veratec, Inc. Walpole, Mass.; Novonet® 149–191, a thermo-bonded grid patterned material containing about 69% rayon, about 25% polypropylene, and about 6% cotton, and having a basis weight of about 100 gsy, available from Veratec, Inc. Walpole, Mass.; HEF Nubtex® 149–801, a nubbed, apertured hydroentangled material, containing about 100% polyester, and having a basis weight of about 70 gsy, available from Veratec, Inc. Walpole, Mass.; Keybak® 951V, a dry formed apertured material, containing about 75% rayon, about 25% acrylic fibers, and having a basis weight of about 43 gsy, available from Chicopee, New Brunswick, N.J.; Keybak® 1368, an apertured material, containing about 75% rayon, about 25% polyester, and having a basis weight of about 39 gsy, available from Chicopee, New Brunswick, N.J.; Duralace® 1236, an apertured, hydroentangled material, containing about 100% rayon, and having a basis weight from about 40 gsy to about 115 gsy, available from Chicopee, New Brunswick, N.J.; Duralace® 5904, an apertured, hydroentangled material, containing about 100% polyester, and having a basis weight from about 40 gsy to about 115 gsy, available from Chicopee, New Brunswick, N.J.; Chicopee® 5763, a carded hydroapertured material (8×6 apertures per inch), containing about 70% rayon, about 30% polyester, and a optionally a latex binder (EVA) of up to about 5% w/w, and having a basis weight from about 75 gsy to about 63 gsy, available form Chicopee, New Brunswick, N.J.; Chicopee® 9900 series (e.g., Chicopee 9931-52 gsy, 50/50 rayon/polyester, and Chicopee 9950-42 gsy, 50/50 rayon/polyester), a carded, hydroentangled material, containing a fiber composition of from 50% rayon and 50% polyester to 100% polyester, and having a basis weight of from about 30 gsy to about 70 gsy, available form Chicopee, New Brunswick, N.J.; Sontara 8868, a hydroentangled material, containing about 50% cellulose and about 50% polyester, and having a basis weight of about 60 gsy, available from Dupont Chemical Corp.

Alternatively, the water insoluble substrate can be a polymeric mesh sponge as described in European Patent No. EP 702550 A1 published Mar. 27, 1996, incorporated by reference herein in its entirety. The polymeric sponge comprises a plurality of plies of an extruded tubular netting mesh prepared from a strong flexible polymer, such as addition polymers of olefin monomers and polyamides of polycarboxylic acids. Although these polymeric sponges are designed to be used in conjunction with a liquid cleanser, these types of sponges can be used as the water insoluble substrate in the present invention.

The substrate can be made into a wide variety of shapes and forms including flat pads, thick pads, thin sheets, ball-shaped implements, irregularly shaped implements, and having sizes ranging from a surface area of about a square inch to about hundreds of square inches. The exact size will depend upon the desired use and product characteristics. Especially convenient are square, circular, rectangular, or oval pads having a surface area of from about 1 $in^2$ to about 144 $in^2$, preferably from about 10 $in^2$ to about 120 $in^2$, and more preferably from about 30 $in^2$ to about 80 $in^2$, and a thickness of from about 1 mil to about 500 mil, preferably from about 5 mil to about 250 mil, and more preferably from about 10 mil to about 100 mil.

The water insoluble substrates of the present invention can comprise two or more layers, each having different textures, abrasiveness, and extensibilities. The differing textures can result from the use of different combinations of materials or from the use of different manufacturing processes or a combination thereof. A dual textured substrate can be made to provide the advantage of having a more abrasive side for exfoliation and a softer, absorbent side for gentle cleansing. Furthermore, the substrate can be a laminate of two layers having differing wet extensibilities. Such laminate substrates are exemplified in copending U.S. application Ser. No. 09/1013,640, filed Jan. 26, 1998, which application is herein incorporated by reference in its entirety. In addition, separate layers of the substrate can be manufactured to have different colors, thereby helping the user to further distinguish the surfaces. Furthermore, it is desirable for the substrates of the present invention to have rounded corners. This feature prevents the tendency of water to accumulate at the corners of an unrounded square substrate.

LATHERING SURFACTANT

The articles of the present invention comprise enough of a lathering surfactant to generate $\geq 30$ ml of Lather Volume (medium hardness water at 95° C.) according to the Lather Volume Test described herein. Preferably, the articles of the present invention comprise from about 0.5% to about 40%, more preferably from about 0.75% to about 12.5%, and most preferably from about 1% to about 11%, based on the weight of the water insoluble substrate, of a lathering surfactant.

By a lathering surfactant is meant a surfactant, which when combined with water and mechanically agitated generates a foam or lather sufficient to cause the article, as a whole, to lather. Preferably, these surfactants or combinations of surfactants should be mild, which means that these surfactants provide sufficient cleansing or detersive benefits but do not overly dry the skin or hair, and yet meet the lathering criteria described above.

A wide variety of lathering surfactants are useful herein and include those selected from the group consisting of anionic lathering surfactants, nonionic lather surfactants, amphoteric lathering surfactants, and mixtures thereof. Generally, the lathering surfactants do not strongly interfere with deposition of the conditioning agents, e.g., are fairly water soluble, and usually have an HLB value of above 10. Cationic surfactants can also be used as optional components, provided they do not negatively impact the overall lathering characteristics of the required, lathering surfactants.

Anionic Lathering Surfactants

Nonlimiting examples of anionic lathering surfactants useful in the compositions of the present invention are disclosed in McCutcheon's, *Deterrents and Emulsifiers*, North American edition (1986), published by allured Publishing Corporation; McCutcheon's, *Functional Materials*, North American Edition (1992); and U.S. Pat. No. 3,929,678, to Laughlin et al., issued Dec. 30, 1975 all of which are incorporated by reference herein in their entirety.

A wide variety of anionic lathering surfactants are useful herein. Nonlimiting examples of anionic lathering surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred The alkoyl isethionates typically have the formula $RCO-OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Other useful anionic materials include phosphates such as monoalkyl, dialkyl, and trialkylphosphate salts.

Other anionic materials include alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and alkanolamine (e.g., triethanolamine), a preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates which are based on taurine, which is also known as 2-aminoethanesulfonic acid. Especially useful are taurates having carbon chains between $C_8$ and $C_{16}$. Examples of taurates include N-alkyltaurines such as the one prepared by reacting dodecylamine with sodium isethionate according to the teaching of U.S. Pat. No. 2,658,072 which is incorporated herein by reference in its entirety. Further nonlimiting examples include ammonium, sodium, potassium and alkanolamine (e.g., triethanolamine) salts of lauroyl methyl taurate, myristoyl methyl taurate, and cocoyl methyl taurate.

Also useful are lactylates, especially those having carbon chains between $C_8$ and $C_{16}$. Nonlimiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are glutamates, especially those having carbon chains between $C_8$ and $C_{16}$. Nonlimiting examples of glutamates include ammonium, sodium, potassium and alkanolamine (e.g., triethanolamine) salts of lauroyl glutamate, myristoyl glutamate, and cocoyl glutamate.

Nonlimiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof Especially preferred for use herein is ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Nonionic Lathering Surfactants

Nonlimiting examples of nonionic lathering surfactants for use in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Alkyl glucosides and alkyl polyglucosides are useful herein, and can be broadly defined as condensation articles of long chain alcohols, e.g. C8-30 alcohols, with sugars or starches or sugar or starch polymers, i.e., glycosides or polyglycosides. These compounds can be represented by the formula $(S)_n$—O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; R is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_1$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G. B. Pat. Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott issued Dec. 25, 1934; which are incorporated herein by reference in their entirety.

Other examples of nonionic surfactants include amine oxides. Amine oxides correspond to the general formula $R_1R_2R_3NO$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

Nonlimiting examples of preferred nonionic surfactants for use herein are those selected form the group consisting of C8–C14 glucose amides, C8–C14 alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

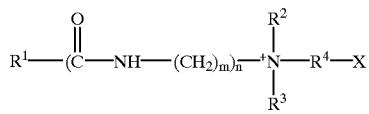

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine)

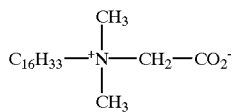

Cocamidopropylbetaine

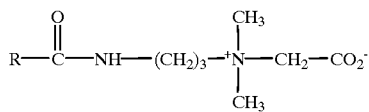

wherein R has from about 9 to about 13 carbon atoms

Cocamidopropyl hydroxy sultaine

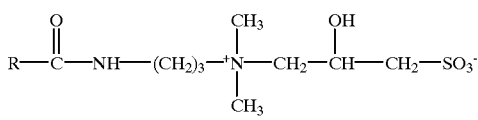

wherein R has from about 9 to about 13 carbon atoms,

Examples of other useful amphoteric surfactants are alkyliminoacetates, and iminodialkanoates and aminoalkanoates of the formulas $RN[CH_2)_mCO_2M]_2$ and $RNH(CH_2)_mCO_2M$ wherein m is from 1 to 4, R is a $C_8$–$C_{22}$ alkyl or alkenyl and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, and mixtures thereof; wherein the nonionic lathering surfactant is selected from the group consisting of lauramine oxide, cocoamine oxide, decyl polyglucose, lauryl polyglucose, sucrose cocoate, C12–14 glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

Lather Volume Test

The articles of the present invention comprise enough of the lathering surfactant to generate greater than about 30 ml, preferably greater than about 50 ml, more preferably greater than about 75 ml, and most preferably greater than about 150 ml of Average Lather Volume. The Average Lather Volume is a measurement determined by the Lather Volume Test. This test provides a consistent volume measurement of the lather/foam generated by the articles described herein. The Lather Volume Test protocol is described as follows:

(1) Hands are washed with Ivory bar before conducting the test. This step removes any soils which may affect the accuracy of the measurement.

(2) The test article is held open in the non-dominant hand with the edges turned up.

(3) 10 m. of water (medium hardness of about 8–10 grains per gallon) at 95° C. is added onto the test article via a 10 cc syringe or a Brinkmann repipetter.

(4) The lather is then generated by rubbing the test article with the dominant hand in a circular motion between the palms for 6 seconds (~2 rotations per second), using moderate pressure (e.g., 4 oz.), and allowing the article to ball-up between the palms of the hand.

(5) The test article is then held open in the non-dominant hand and an additional 10 ml of water (medium hardness of about 8–10 grains per gallon) at 95° C. is added onto the test article via a 10 cc syringe or a Brinkmann repipetter. The wetted article is again rubbed with the dominant had (3 rotations) using moderate force (e.g, 4 oz.) so that the test article becomes balled-up between the palms.

(6) The test article is then opened and rubbed 5 times by holding one edge of the article in one hand and rotating the hand holding the other side to further activate lather.

(7) The test article is then flipped over and Step #6 is repeated using the other hand.

(8) The lather is gathered by holding the test article in a cupped hand and scraping the lather off the test article with the other hand, being careful to only scrape lather form the test article. The lather from the test article is placed into a graduated cylinder or beaker big enough to hold the generated lather. This procedure is repeated 5 times on the same test article, and the lather from each iteration is accumulated in the same graduated cylinder or beaker. The total accumulated lather from these iterations is designated as the Lather Volume.

(9) To achieve consistent results, the Average Lather Volume is reported as the average of three test sample replications of Steps 1–8.

SKIN CARE ACTIVE COMPONENT

The personal cleansing articles of the present invention essentially comprise a safe and effective amount of a skin care active component which comprises at least one skin care active selected from the group consisting of water soluble skin care actives, oil soluble skin care actives, pharmaceutically-acceptable salts and mixtures thereof. The term "skin care active," as used herein, means personal care actives which can be used to deliver a benefit to the skin and/or hair and which generally are not used to confer a conditioning benefit, as hereinafter defined. The term "safe and effective amount" as used herein, means an amount of a skin care active ingredient high enough to modify the condition to be treated or to deliver the desired skin care benefit, but low enough to avoid serious side effects, at a reasonable benefit to risk ratio within the scope of sound medical judgment. The term "skin care benefit," as used herein, means the therapeutic, prophylactic, and/or chronic benefits associated with treating a particular condition with one or more of the skin care actives described herein. What is a safe and effective amount of the skin care active ingredient will vary with the specific skin care active, the ability of the active to penetrate through the skin, the age, health condition, and skin condition of the user, and other like factors. Preferably the articles of the present invention comprise from about 0.001% to about 50%, more preferably from about 0.01% to about 25%, even more preferably 0.05% to about 10%, and most preferably 0.1% to about 5%, by weight of the water insoluble substrate, of the skin care active component.

The skin care active component of the present invention can comprise: a water soluble skin care active, an oil soluble skin care active, a skin care emulsion, or any combination or permutation of the three. The oil soluble skin care active is selected from one or more oil soluble skin care actives such that the weighted arithmetic mean solubility parameter of the oil soluble skin care active is less than or equal to 10.5. The water soluble skin care active is selected from one or more water soluble skin care active such that the weighted arithmetic mean solubility parameter of the water soluble conditioning agent is greater than 10.5. It is recognized, based on this mathematical definition of solubility parameters, that it is possible, for example, to achieve the required weighted arithmetic mean solubility parameter, i.e. less than or equal to 10.5, for an oil soluble skin care active comprising two or more compounds if one of the compounds has an individual solubility parameter greater than 10.5. Conversely, it is possible to achieve the appropriate weighted arithmetic mean solubility parameter, i.e. greater than 10.5, for a water soluble skin care active comprising two or more compounds if one of the compounds has an individual solubility parameter less than or equal to 10.5.

Solubility parameters are well known to the formulation chemist of ordinary skill in the art and are routinely used as a guide for determining compatibilities and solubilities of materials in the formulation process. The solubility parameter of a chemical compound, $\delta$, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[\frac{\sum_i E_i}{\sum_i m_i}\right]^{1/2}$$

wherein $\Sigma_i E_i$=the sum of the heat of vaporization additive group contributions, and $\Sigma_i m_i$=the sum of the molar volume additive group contributions Standard tabulations of heat of vaporization and molar volume additive group contributions for a wide variety of atoms and groups of atoms are collected in Barton, A. F. M. *Handbook of Solubility Parameters*, CRC Press, Chapter 6, Table 3, pp. 64–66 (1985), which is incorporated by reference herein in its entirety. The above solubility parameter equation is described in Fedors, R. F., "A Method for Estimating Both the Solubility Parameters and Molar Volumes of Liquids", *Polymer Engineering and Science*, vol. 14, no. 2, pp. 147–154 (February 1974), which is incorporated by reference herein in its entirety.

Solubility parameters obey the law of mixtures such that the solubility parameter for a mixture of materials is given by the weighted arithmetic mean (i.e. the weighted average) of the solubility parameters for each component of that mixture. See, *Handbook of Chemistry and Physics*, 57th edition, CRC Press, p. C-726 (1976–1977), which is incorporated by reference herein in its entirety. Formulation chemists typically report and use solubility parameters in units of $(cal/cm^3)^{1/2}$. The tabulated values of additive group contributions for heat of vaporization in the *Handbook of Solubility Parameters* are reported in units of kJ/mol. However, these tabulated heat of vaporization values are readily converted to cal/mol using the following well-known relationships:

1 J/mol=0.239006 cal/mol and 1000 J=1 kJ.

See Gordon, A. J. et al., *The Chemst's Companion*, John Wiley & Sons, pp. 456–463, (1972), which is incorporated by reference herein in its entirety. Solubility parameters have also been tabulated for a wide variety of chemical materials. Tabulations of solubility parameters are found in the above-cited *Handbook of Solubility Parameters*. Also, see "Solubility Effects In Product, Package, Penetration, And Preservation", C. D. Vaughan, *Cosmetics and Toiletries*, vol. 103, October 1988, pp. 47–69, which is incorporated by reference herein in its entirety. Using the information hereinbefore described, the formulation chemist of ordinary skill in the art can determine the solubility parameters of the skin care active ingredients hereinafter described.

The skin care active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Furthermore, pharmaceutically-acceptable salts of these active ingredients are also useful herein. The following active ingredients are useful in the compositions of the present invention.

A wide variety of skin care active ingredients are useful herein and include those selected from the group consisting of anti-acne actives, anti-wrinkle and anti-skin atrophy actives, skin barrier repair aids, cosmetic soothing aids, topical anesthetics, artificial tanning agents and accelerators, skin lightening actives, antimicrobial and antifungal actives, sunscreen actives, sebum stimulators, sebum inhibitors, and mixtures thereof.

Anti-Acne Actives:

Anti-acne actives can be effective in treating *acne vulgaris*, a chronic disorder of the pilosebaceous follicles. The condition involves inflammation of the pilosebaceous apparatus thereby resulting in lesions, which may include papules, pustules, cysts, comedomes, and severe scarring. The bacteria *Corynebacterium acnes* and *Staphylococcus epidermidis* are usually present in the pustular contents.

Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids and bioflavonoids; bile salts such as scymnol sulfate and its derivatives, deoxycholate, and cholate; abietic acid; adapalene; allantoin; aloe extracts; arbietic acid and its salts; aryl-2,4 dioxo oxazolidine derivatives; ASEBIOL (available from Laboratories Serobiologiques, located in Somerville, N.J.); azaleic acid; barberry extracts; bearberry extracts; belamcanda chinensis; benzoquinolinones; benzoyl peroxide; berberine; BIODERMINE (available from Sederma, located in Brooklyn, N.Y.); bioflavinoids; bisabolol; S-carboxymethyl cysteine; carrot extracts; cassin oil; clove extracts; citral; citronellal; climazole; Completech MBAC-OS (available from Lipo); CREMOGEN M82 (available from Dragoco, located in Totowa, N.J.); cucumber extracts; dehydroacetic acid and its salts; dehydroeplandersterone salicylate; dichlorophenyl imidazoldioxolan which is commercially available as COMPLETECH MBAC-OS (from Lipo, located in Paterson, N.J.); DL valine and its esters; DMDM hydantoin; Epicutin TT (available from CLR); erythromycin; escinol; ethyl hexyl monoglyceryl ether; ethyl 2-hydroxy undecanoate; farnesol; farnesol acetate; geranoil; glabridin; gluconic acid; gluconolactone; glyceryl monocaprate; glycolic acid; grapefruit seed extract; gugu lipid; Hederagenin (available from Maruzen); hesperitin; hinokitol; hops extract; hydrogenated rosin; 10 hydroxy decanoic acid; ichtyhol; interleukin 1 alpha antagonists; iodo-2-propynyl butyl carbamate; Kapilarine (available from Greentech); ketoconazole; lactic acid; lemon grass oil; Lichochalcone LR15 (available from Maruzen); linoleic acid; LIPACIDE C8CO (available from Seppic, located in Paris, France); lovastatin; 4 methoxysalicylic acid; metronidazole; minocycline; mukurossi; neem seed oil; vitamin $B_3$ compounds (such as niacinamide and nicotinic acid); nisin; 5-octanoly salicylic acid; octopirox; panthenol; 1-pentadecanol; peonia extract; peppermint extract; phelladendron extract; 2-phenyl-benzothiophene derivatives; phloretin; PHLOROGINE (available from Secma); phosphatidyl choline; proteolytic enzymes; quercetin; red sandalwood extract; resorcinol; rosemary extract; rutin; sage extract; salicin; salicylic acid; skull cap extract; siber hegner extract; siberian saxifrage extract; silicol; sodium lauryl sulfate; sodium sulfoacetamide; Sophora Extract (available from Maruzen); sorbic acid; sulfur; sunder vati extract; tea tree oil; tetracyline; tetra hydroabietic acid; thyme extract; tioxolone; tocopherol; trehalose 6-undecylenoate; 3 tridecene-2-ol; triclosan; tropolone; UNITRIENOL T27 (available from Unichem, located in Gouda, Netherlands); vitamin $D_3$ and its analogs; white thyme oil; willow bark extract; wogonin; Ylang Ylang; zinc glycerolate; zinc linoleate; zinc oxide; zinc pyrithione; zinc sulfate and mixtures thereof Antimicrobial and Antifungal Actives:

Antimicrobial and antifungal actives can be effective to prevent the proliferation and growth of bacteria and fungi. Nonlimiting examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentarnidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione; clotrimazole; alantolactone; isoalantolactone; alkanet extract (alaninin); anise; arnica extract (helenalin acetate and 11, 13 dihydrohelenalin); Aspidium extract (phloro, lucinol containing extract); barberry extract (berberine chloride); bay sweet extract; bayberry bark extract (myricitrin); benzalkonium chloride; benzethonium chloride; benzoic acid and its salts; benzoin; benzyl alcohol; blessed thistle; bletilla tuber; bloodroot; bois de rose oil; burdock; butyl paraben; cade oil; CAE (available from Ajinomoto, located in Teaneck, N.J.); cajeput oil; Cangzhu; capsicum frutescens extract; caraway oil; cascarilla bark (sold under the tradename ESSENTIAL OIL); cedarleaf oil; chamomille; chaparral; chlorhexidine gluconate; chlorophenesin; chlorxylenol; cinnamon oil; citronella oil; clove oil; Crinipan AD (available from Climbazole); 2,3-dihydro-farnesol; dehydroacetic acid and its salts; dill seed oil; DOWICIL 200 (available from Dow Chemical, located in Midland, Mich.); echinacea; elenolic acid; epimedium; ethyl paraben; Fo-Ti; galbanum; garden bumet; GERMALL 115 and GERMALL II (available from ISP-Sutton Labs, located in Wayne, N.J.); German chamomile oil; giant knotweed; GLYDANT (available from Lonza, located in Fairlawn, N.J.); GLYDANT PLUS (available from Lonza); grapefruit seed oil; 1,6 hexanediol; hexamidine diisethionate; hinokitiol; honey; honeysuckle flower; hops; immortelle; iodopropynl butyl carbamide (available from Lonza); isobutyl paraben; isopropyl paraben; JM ACTICARE (available from Microbial Systems International, located in Nottingham, NG); juniper berries; KATHON CG (available from Rohm and Haas, located in Philadelphia, Pa.); kojic acid; labdanum; lavender; lemon balm oil; lemon grass; methyl paraben; mint; mume; mustard; myrrh; neem seed oil; ortho phenyl phenol; olive leaf extract (available from Bio Botanica); parsley; patchouly oil; peony root; 1,2 pentandiol; PHENONIP (available from Nipa Labs, located in Wilmington, Del.); phenoxyethanol; phytosphingosine; pine needle oil; PLANSERVATIVE (available from Campo Research); propyl paraben; purslane; quillaira; rhubarb; rose geranium oil; rosemary; sage; salicylic acid; sassafras; savory; sichuan lovage; sodium meta bisulfite; sodium sulfite; SOPHOLIANCE (available from Soliance, located in Compiegne, France); sorbic acid and its salts; sphingosine; stevia; storax; sucrose esters; tarmic acid; tea; tea tree oil (cajeput oil); thyme; triclosan; triclocarban; tropolone; turpentine; umbelliferone (antifungal); yucca; and mixtures thereof.

Anti-Wrinkle, Anti-Skin Atrophy and Skin Repair Actives:

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include retinoic acid and its derivatives (e.g., cis and trans); retinal; retinol; retinyl esters such as retinyl acetate, retinyl palmitate, and retinyl propionate; vitamin $B_3$ compounds (such as niacinamide and nicotinic acid), salicylic acid and derivatives thereof (such as 5-octanoyl salicylic acid, heptyloxy 4 salicylic acid, and 4-methoxy salicylic acid); sulfur-containing D and L amino acids and their derivatives and salts, particularly the N-acetyl derivatives, a preferred example of which is N-acetyl-L-cysteine; thiols, e.g. ethane thiol; hydroxy acids, phytic acid, lipoic acid; lysophosphatidic acid; skin peel agents (e.g., phenol and the like); Actein 27-Deoxyactein Cimicifugoside (available from Cirnigoside); adapalene; ademethionine; adenosine; aletris extract; alkyl glutathione esters; alkoxyalkoxy alkoxyn benzoic and derivatives; aloe derived lectins; amino propane phosphoric acid; 3-aminopropyl dihydrogen phosphate; Amadorine (available from Barnet Products); anise extracts; AOSINE (available from Secma); arginine amino benzoate; ASC III (available from E. Merck, located in Darmstadt, Germany); ascorbic acid; ascorbyl palmitate; asiatic acid; asiaticosides; ARLAMOL GEO™ (available from ICI, located in Wilmington, Del.); azaleic acid; benzoic acid derivatives; bertholletia extracts; betulinic acid; BIOCHANIN A AND BIOPEPTIDE CL (available from Sederma, located in Brooklyn, N.Y.); BIOPEPTIDE EL (available from Sederma); biotin; blackberry bark extract; blackberry lily extracts; black cohosh extract; blue cohesh extract; butanoyl betulinic acid; carboxymethyl 1,3 beta glucan; catecholamnines; chalcones; citric acid esters; chaste tree extract; clover extracts; coumestrol; CPC Peptide (available from Barnet Products); daidzein; dang gui extract; darutoside; debromo laurinterol; 1-decanoyl-glycero-phosphonic acid; dehydrocholesterol; dehydrodicreosol; dehydrodieugenol; dehydroepiandersterone; DERMOLECTINE (available from Sederma); dehydroascorbic acid; dehydroepiandersterone sulfate; dianethole; dihydroxy benzoic acid; 2,4 dihydroxybenzoic acid; diglycol guanidine succinate; diosgenin; disodium ascorbyl phosphate; dodecanedioic acid; Ederline (available from Seporga); Enderline (available from Laboratories Seporga); equol; eriodictyol; estrogen and its derivatives; ETF (available from Laboratories Seporga); ethocyn; ELESERYL SH (available from Laboratories Serobiologiques, located in Somerville, N.J.); ENDONUCLEINE (available from Laboratories Serobiologiques); ergosterol; eythrobic acid; fennel extract; fenugreek seed extract; FIBRASTIL (available from Sederma); FIBROSTIMULINES S and P (available from Sederma); FIRMOGEN LS 8445 (available from Laboratories Serobiologiques); formononetin; forsythia fruit extract; gallic acid esters; gamma amino butyric acid; GATULINE RC (available from Gattlefosse, located in Priest, France); genistein; genisteine; genistic acid; gentisyl alcohol; gingko bilboa extracts; ginseng extracts; ginsenoside (RO, $R_{6-1}$, $R_{6-2}$, $R_{6-3}$, $R_C$, $R_D$, $R_E$, $R_F$, $R_{F-2}$, $R_{G-1}$, $R_{G-2}$); gluco pyranosyl-L-ascorbate; glutathione and its esters; glycitein; hesperitin; hexahydro curcumin; HMG- coenzyme A reductase inhibitors; hops extracts; 11 hydroxy undecanoic acid; 10 hydroxy decanoic acid; 25-hydroxycholesterol; 7-hydroxylated sterols; hydroxyethyl isostearyloxy isopropanolamine; hydroxy-tetra methyl piperidinyloxy; hypotaurine; ibukijakou extract; isoflavone SG 10 (available from Barnet Products); kinetin; kohki extract; L-2-OXO-thiazolidine-4-carboxylic acid esters; lactate dehydrogenase inhibitors; 1-lauryl, -lyso-phosphatidyl choline; lectins; lichochalcone LF15 (available from Maruzen); licorice extracts; lignan; lumisterol; lupenes; luteolin; lysophosphitidic acid; magnesium ascorbyl phosphate; margin; melatonin; melibiose; metalloproteinase inhibitors; methoprene; methoprenic acid; mevalonic acid; MPC COMPLEX (available from CLR); N methyl serine; N methyl taurine; N, $N^1$-bis (lactyl) cysteamine; naringenin; neotigogenin; o-desmethylangoiensin; oat beta glucan; oleanolic acid; pantethine; phenylalanine; photoanethone; piperdine; placental extracts; pratensein; pregnenolone; pregnenolone acetate; pregnenolone succinate; premarin; quillaic acid; raloxifene; REPAIR FACTOR 1 and REPAIR FACTOR FCP (both available from Sederna); retinoates (esters of $C_2$–$C_{20}$ alcohols); retinyl glucuronate; retinyl linoleate; S-carboxymethyl cysteine; SEANAMINE FP (available from Laboratories Serobiologiques); sodium ascorbyl phosphate; soya extracts; spleen extracts; tachysterol; taurine; tazarotene; tempol; thymulen; thymus extracts; thyroid hormones; tigogenin; tocopheryl retinoate; toxifolin; traumatic acid; tricholine citrate; trifoside; uracil derivatives; ursolic acid; vitamin $D_3$ and its analogs; vitamin K; vitex extract; yam extract; yamogenin; zeatin; and mixtures thereof.

Skin Barrier Repair Actives:

Skin barrier repair actives are those skin care actives which can help repair and replenish the natural moisture barrier function of the epidernis. Nonlimiting examples of skin barrier repair actives include Alpha Lipid (available from Lucas Meyer); ascorbic acid; biotin; biotin esters; brassicasterol; caffeine; campesterol; canola derived sterols; Cennamides (available from Ennagram); Ceramax (available from Alban Muller); CERAMAX (available from Quest, located in Ashford, England); CERAMIDE 2 and CERAMIDE HO3™ (both available from Sederma); CERAMIDE II (available from Quest); CERAMIDE III and IIIB (both available from Cosmoferm, located in Deft, Netherlands); CERAMIDE LS 3773 (available from Laboratories Serobiologiques); CERAMINOL (available from Inocosm); Cerasol and Cephalip (both available from Pentapharm); cholesterol; cholesterol hydroxystearate; cholesterol isostearate; 7 dehydrocholesterol; DERMATEIN BRC and DERMATEIN GSL (both available from Hormel); ELDEW CL 301 AND ELDEW PS 203 (both available from Ajinomoto); Fitobroside (available from Pentapharm); galactocerebrosides; Generol 122 (available from Henkel); glyceryl serine amide; hydroxyethyl isostearyl isopropanolamine; lactic acid; Lactomide (available from Pentapharm); lanolin; lanolin alcohols; lanosterol; lauric acid N laurylglucamide; lipoic acid; N-acetyl cysteine; N-acetyl-L-serine; N-methyl-L-Serine; Net Sterol-ISO (available from Barnet Products); vitamin B3 compounds (such as niacinamide and nicotinic acid); palmitic acid; panthenol; panthetine; phosphodiesterase inhibitors; PHYTO/CER (available from Intergen); phytoglycolipid millet extract (available from Barnet Products Distributer, located in Englewood, N.J.); PHYTOSPHINGOSINE (available from Gist Brocades, located in King of Prussia, Pa.); PSENDOFILAGGRIN (available from Brooks Industries, located in South Plainfield, N.J.); QUESTAMIDE H (available from Quest); serine; sigmasterol; sitosterol; soybean derived sterols; sphingosine; sphingomylinase; S-lactoyl glutathione; stearic acid; Structurine (available from Silah); SUPER STEROL ESTERS (available from Croda); thioctic acid; THSC CERAMIDE OIL (available from Campo Research); trimethyl glycine; tocopheryl nicotinate; vitamin $D_3$; Y2 (available from Ocean Pharmaceutical); and mixtures thereof.

Non-steroidal Cosmetic Soothing Actives:

Cosmetic soothing actives can be effective in preventing or treating inflammation of the skin. The soothing active enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency. Nonlimiting examples of cosmetic soothing agents include the following categories: propionic acid derivatives; acetic acid derivatives; fenamic acid derivatives; biphenylcarboxylic acid derivatives; and oxicams. All of these cosmetic soothing actives are fully descnbed in U.S. Pat. No. 4,985,459 to Sunshine et al., issued Jan. 15, 1991, incorporated by reference herein in its entirety. Nonlimiting examples of useful cosmetic soothing actives include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucloxic acid, absinthium, acacia, aescin, alder buckthorn extract, allantoin, aloe, APT (available from Centerchem), arnica, astragalus, astragalus root extract, azulene, Baicalin SR 15 (available from Barnet Products Dist.), baikal skullcap, baizhu, balsam canada, bee pollen, BIOPHYTEX (available from Laboratories Serobiologiques), bisabolol, black cohosh, black cohosh extract blue cohosh, blue cohosh extract, boneset, borage, borage oil, bradykinin antagonists, bromelain, calendula, calendula extract, Canadian Willowbark Extract (available from Fytokem), candelilla wax, Cangzhu, canola phytosterols, capsicum, carboxypeptidase, celery seed, celery stem extract, CENTAURIUM (available from Sederma), centaury extract, chamazulene, chamomile, chamomile extract, chaparral, chaste tree, chaste tree extract, chickweed, chicory root, chicory root extract, chirata, chishao, collodial oatmeal, comfrey, comfrey extract, CROMOIST CM GLUCAN (available from Croda), darutoside, dehurian angelica, devil's claw, divalent metals (such as, magnesium, strontium, and manganese), doggrass, dogwood, Eashave (available from Pentapharm), eleuthero, ELHIBIN (available from Pentapharm), ENTELINE 2 (available from Secma), ephedra, epimedium, esculoside; ethacrynic acid, evening primrose, eyebright, Extract LE-100 (available from Sino Lion), Fangfeng, feverfew, ficin, forsythia fruit, Fytosterol 85 (available from Fytokem), ganoderma, gaoben, Gatuline A (available from Gattefosse), gentian, germanium extract, gingko bilboa extract, ginkgo, ginseng extract, goldenseal, gorgonian extract, gotu kola, grape fruit extract, guaiac wood oil, guggal extract, helenalin esters, henna, honeysuckle flower, horehound extract, horsechestnut, horsetail, huzhang, hypericum, ichthyol, immortelle, ipecac, job's tears, jujube, kola extract, LANACHRYS 28 (available from Lana Tech), lemon oil, lianqiao, licorice root, ligusticum, ligustrum, lovage root, luffa, mace, magnolia flower, manjistha extract, margaspidin, matricin, melatonin, MICROAT IRC (available from Nurture), mints, mistletoe, Modulene (available from Seporga), mono or diglucosides of glabridin, mono or diglucosides of gentisin, MTA (5'-deoxy-5'-methythioadenosine), mung bean extract, musk, N-methyl arginine, oat beta glucan, oat extract, orange, panthenol, papain, phenoxyacetic acid, peony bark, peony root, Phytoplenolin (available from Bio Botanica), phytosphingosine, Preregen (available from Pentapharm), purslane, QUENCH T (available from Centerchem), quillaia, red sage, rehmannia, rhubarb, rosemary, rosmarinic acid, royal jelly, rue, rutin, sandlewood, sanqi, sarsaparilla, saw palmetto, SENSILINE (available from Silab), SIEGESBECKIA (available from Sederma), stearyl glycyrrhetinate, Stimutex (available from Pentapharm), storax, strontium nitrate, sweet birch oil, sweet woodruff, tagetes, tea extract, thyme extract, tienchi ginseng, tocopherol, tocopheryl acetate, triclosan, turmeric, urimei, ursolic acid, white pine bark, witch hazel xinyi, yarrow, yeast extract, yucca, and mixtures thereof.

Artificial Tanning Actives and Accelerators.

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; acetyl tyrosine; phospho-DOPA; brazilin; caffeine; coffee extracts; dihydroxyacetone; DNA fragments; isobutyl methyl xanthine; methyl xanthine; Phototan (available from Laboratoires Serobiologiques); prostaglandins; tea extracts; theophylline; tyrosine; UNIPERTAN P2002 and UNIPERTAN P27 (both available from Unichem); and mixtures thereof.

Skin Lightening Actives:

Skin lightening actives can actually decrease the amount of melanin in the skin or provide an such an effect by other mechanisms. Skin lightening actives suitable for use herein are described in copending patent application Ser. No. 08/479,935, filed on Jun. 7, 1995 in the name of Hillebrand, corresponding to PCT Application No. U.S. Ser. No. 95/07432, filed Jun. 12, 1995; and copending patent application Ser. No. 08/390,152, filed on Feb. 24, 1995 in the names of Kalla L. Kvalnes, Mitchell A. DeLong, Barton J. Bradbury, Curtis B. Motley, and John D. Carter, corresponding to PCT Application No. U.S. Ser. No. 95/02809, filed Mar. 1, 1995, published Sep. 8, 1995; all incorporated herein by reference. Nonlimiting examples of skin lightening actives useful herein include adapalene, aloe extract, alpha-glycaryl-L-ascorbic acid, aminotyroxine, ammonium lactate, anethole derivatives, apple extract, arbutin, areca catechu L. extract, ascorbic acid, ascorbyl palmitate, azelaic acid, bamboo extract, bearberry extract, bletilla tuber, bupleurum falcatum extract, burnet extract, Burnet Power (available from Barnet Products), butyl hydroxy anisole, butyl hydroxy toluene, butyl resoreinol, Chuanxiong, cola decaballo extract, Dang-Gui, deoxyarbutin, 1,3 diphenyl propane derivatives, 2,5 dihydroxybenzoic acid and its derivatives, 2-(4-acetoxyphenyl)-1,3 dithane, 2-(4-hydroxyphenyl)-1,3 dithane, ellagic acid, escinol, estragole derivatives, esculoside, esculetin, FADEOUT (available from Pentapharm), Fangfeng, fennel extract, gallic acid and its derivatives, ganodenna extract, gaoben, GATULINE WHITENING (available from Gattlefosse), genistic acid and its derivatives, gentisyl alcohol, glabridin and its derivatives, gluco pyranosyl-1-ascorbate, gluconic acid, glucosamine, glycolic acid, glycyrrhizinic acid, green tea extract, 4-Hydroxy-5-methyl-3[2H]-furanone, hydroquinine, 4 hydroxyanisole and its derivatives, 4-hydroxy benzoic acid derivatives, hydroxycaprylic acid, hyptis extract, inositol ascorbate, kojic acid, kojic dipalnitate, lactic acid, lemon extract, licorice extract, Licorice P-TH (available from Barnet Products), linoleic acid, magnesium ascorbyl phosphate, Melfade (available from Pentapharm), MELAWHITE (available from Pentapharm), Melanostatine DM (available from Laboratories Seporga), morus alba extract, mulberry root extract, niacinamide, 5-octanoyl salicylic acid, parsley extract, phellinus linteus extract, pinon blanco extract, pinon negro extract, piri-piri extract, pyrogallol derivatives, retinoic acid, retinol, retinyl esters (acetate, propionate, palmitate, linoleate), 2,4 resorcinol derivatives, 3,5 resorcinol derivatives, rose fruit extract, rucinol, salicylic acid, Song-Yi extract, Sophora Powder (available from Barnet Products), 4-thioresorein, 3,4,5 trihydroxybenzyl derivatives, tranexamic acid, tyrostat (Rumex Extract available from Fytokem), Tyroslat 10,11 (available from Fytokem), vanilla derivatives, vitamin $D_3$ and its analogs, and mixtures thereof.

Sunscreen Actives:

Also useful herein are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. Still other useful sunscreens include aminobenzoic acid (PABA), benzylidene camphor, butyl methoxy dibenzoyl methane, diethanolamine p-methoxycinnamate, dioxybenzone, ethyl dihydroxypropyl (PABA), glyceryl aminobenzoate, homomenthyl salicylate, isopropyl dibenzoyl methane, lawsone and dihydroxyacetone, menthyl anthranilate, methyl anthranilate, methyl benzylidene camphor, octocrylene, octyl dimethyl (PABA), octyl methoxycinnamate, oxybenzone, 2-phenylbenzimidazole-5-sulfonic acid, red petrolatum, sulisobenzone, titanium dioxide, triethanolamine salicylate, zinc oxide, and mixtures thereof. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

Exact amounts of sunscreens which can be employed will vary depending upon the sunscreen chosen and the desired Sun Protection Factor (SPF) to be achieved. SPF is a commonly used measure of photoprotection of a sunscreen against erythema. See *Federal Register*, Vol. 43, No. 166, pp. 38206–38269, Aug. 25, 1978, which is incorporated herein by reference in its entirety.

Sebum Stimulators:

Sebum stimulators can increase the production of sebum by the sebaceous glands. These skin care actives are especially useful for post menopausal women who are sebum deficient. Nonlimiting examples of sebum stimulating actives include bryonolic acid, completech MBAC-DS, dehydroetiandrosterone (also known as DHEA), orizanol and mixtures thereof.

Sebum Inhibitors:

Sebum inhibitors can decrease the production of sebum by the sebaceous glands. Nonlimiting examples of sebum inhibiting actives include aluminium hydroxy chloride, ASEBIOL (available from Laboratories Serobiologiques), BIODERMINE (available from Sederma), climbazole, COMPLETECH MBAC-OS (available from Lipo), corticosteroids, cucumber extracts, dehydroacetic acid and its salts, dichlorophenyl imidazoldioxolan (available from Elubiol), gugulipiu, ketoconazole, Lichochalcone LR 15 (available from Maruzen), niacinamide, phloretin, PHLO-ROGINE (available from Secma), Phycosaccharide Anti-Acne (available from Codif), S-carboxylmethyl cysteine, sepicontrol AS, spironolactone, tioxolone, tocopherol, tranexamic acid, UNITRIENOL T27 (available from Unichem), zincidone (UC1B), and mixtures thereof.

Protease Inhibitors:

Also useful as active ingredients in the present invention are protease inhibitors. Nonlimiting examples of protease inhibitors which are useful in the compositions of the present invention are those selected from the group consisting of A E Complex (available from Barnet Products); ALE (available from Seporga); allicin; alpha lupaline; Aosaine (available from Secma); Aprotinin (available from Pentapharm); areca catechu (Betel Nut) extract; areca catechu extracts; Blue Algae Extract (available from Collaborative Labs); Centaurium (available from Sederma); cholesterol sulfate; CMST (available from Bioetica); Dermoprotectine (available from Sederma); Disacoside HF 60 (available from Barnet Products); Elhibin (available from Pentapharm); Fluid Out Colloid (available from Vegetech); Hypotaurine (available from Sogo Pharmaceutical); In Cyte Heathes (available from Collaborative Labs); Micromerol (available from Collaborative Labs); Pefabloc SP (available from Pentapharm); Sepicontrol AS (available from Seppic); Siegesbeckia (available from Sederma); Sophorine (available from Barnet Products); Thiotaine (available from Barnet Products); uncaria gambis roxburgh extract; zinc and mixtures thereof.

Skin Tightening Agents:

Also useful as active ingredients in the present invention are skin tightening agents. Nonlimiting examples of skin tightening agents which are useful in the compositions of the present invention are those selected from the group consisting of Biocare SA (available from Amerchol); egg albumen; Flexan 130 (available from National Starch); Gatuline Lifting (available from Gattefosse); Pentacare HP (available from Pentapharm); Vegeseryl (available from Laboratories Serobioloques) and mixtures thereof.

Anti-Itch Ingredients:

Also useful as active ingredients in the present invention are anti-itch ingredients. Nonlimiting examples of anti-itch ingredients which are useful in the compositions of the present invention are those selected from the group consisting of Stimu-tex (available from Pentapharm); Takanal (available from Ikeda-Distributer); Ichthyol (available from International Sourcing-Distributor); Oxygenated Glyceryl Triesters (available from Seporgia) and mixtures thereof.

Miscellaneous Actives

Miscellaneous actives such as hair growth inhibitors, 5-alpha reductase inhibitors, desquamating enzyme enhancers and anti-glycation agents may also be employed herein. Examples of materials of these types are provided as follows:

Hair Growth Inhibitors:

Nonlimiting examples of hair growth inhibitors which are useful in the compositions of the present invention include 17-beta estradiol, adamantyguanidines, adamantylamidines, adenylosuccinate synthase inhibitors, anti angiogenic steroids, aspartate transcarbamylase inhibitors, betamethasone valerate, bisabolol, copper ions, curcuma extract, cycloxygenase inhibitors, cysteme pathway inhibitors, dehydroacetic acid, dehydroepiandrosterone, diopyros leak extract, epidermal growth factor, epigallocatechin, essential fatty acids, evening primrose oil, gamma glutamyl transpeptidase inhibitors, ginger oil, glucose metabolism inhibitors, glutamine metabolism inhibitors, glutathione, green tea extracts, heparin, Kapilanne (available from International Sourcing Distributor), L, 5 diaminopentanoic acid, L-aspargine synthase inhibitors, linoleic acid, lipoxygenase inhibitors, longa extract, mimosinamine dihydrochloride, mimosine, nitric oxide synthase inhibitors, non-steroidal antiinflamatories, ornithine decarboxylase inhibitors, omthine aminotransferase inhibitors, panthenol, phorhetur, phosphodiesterase inhibitors, pleione extract, protein kinase C inhibitors, salpha reductase inhibitors, sulfhydral reactive compounds, tioxolone, transforming growth factor beta 1, urea, zinc ions and mixtures thereof.

5-Alpha Reductase Inhibitors:

Nonlimiting examples of 5-alpha reductase inhibitors which are useful in the compositions of the present invention include Clove 55 (available from Barnet Products Distributor), ethynylestradiol, genisteine, genistine, licochalcone LR-15, Phycosaccharide Anti-Acne (available from Codif), saw palmetto extracts, Sophora Extract (available from Maruzen), zincidone and mixtures thereof.

Desquamating Enzyme Enhancers:

Nonlimiting examples of desquamating enzyme enhancers which are useful in the compositions of the present invention include alanine, aspastic acid, N methyl serine, serine, trimethyl glycine and mixtures thereof.

Anti-Glycation Agents:

A nonlimiting example of an anti-glycation agent which is useful in the compositions of the present invention would be Amadorine (available from Barnet Products Distributor).

Preferred examples of actives useful herein include those selected from the group consisting of salicylic acid, benzoyl peroxide, 3-hydroxy benzoic acid, glycolic acid, lactic acid, 4-hydroxy benzoic acid, acetyl salicylic acid, niacinamide, cis-retinoic acid, trans-retinoic acid, retinol, retinyl palmitate, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, neocycin sulfate, 2-ethylhexyl p-methoxycinnamic acid, oxybenzone, 2-phenylbenzimidozole-5-sulfonic acid, dihydroxyacetone, panthenol, lactic acid, arbutin, kojic acid, allantoin, cholesterol, $C_{10}$–$C_{30}$ cholesterol/lanosterol esters, tocopherol, tocopheryl acetate, and mixtures thereof.

The skin care active component of the present invention can also comprise a skin care emulsion which is useful for providing a skin care benefit to the skin or hair. The term "skin care emulsion" as used herein means the combination of a discontinuous phase comprising an aqueous component that is enveloped by a continuous phase comprising an oil soluble component. The water soluble component comprises compounds selected from the group consisting of water, water soluble skin care actives, water soluble skin conditioning agents, as hereinafter described, and mixtures thereof. The oil soluble component comprises compounds selected from the group consisting of oil soluble skin care actives, oil soluble skin conditioning agents, as hereinafter described, and mixtures thereof In preferred embodiments, the skin care emulsion would further comprise an emulsifier. The skin care emulsion comprises from about 0.25% to about 150%, preferably from about 0.5% to about 100%, and more preferably from about 1% to about 50% by weight of said water insoluble substrate.

Although an emulsifier capable of forming an emulsion of the discontinuous and continuous phases is preferred in the present invention, it is recognized in the art of skin care formulations that a water soluble skin care active can be enveloped by an oil soluble skin care active without an emulsifier. As long as the water soluble skin care active is enveloped by the oil soluble agent, thereby protected from being rinsed away during the cleansing process, the composition would be within the scope of the present invention.

The discontinuous phase can optionally comprise other water-soluble or dispersible materials that do not adversely affect the stability of the skin care emulsion. One such material is a water-soluble electrolyte. The dissolved electrolyte minimizes the tendency of materials present in the lipid phase to also dissolve in the water phase. Any electrolyte capable of imparting ionic strength to the internal phase can be used. Suitable electrolytes include the water soluble mono-, di- or trivalent inorganic salts such as water-soluble halides, e.g., chlorides, nitrates and sulfates of alkali metals and alkaline earth metals. Examples of such electrolytes include sodium chloride, calcium chloride, sodium sulfate, magnesium sulfate, and sodium bicarbonate. The electrolyte will typically be included in a concentration in the range of from about 1 to about 20% of the discontinuous phase.

Other water-soluble or dispersible materials that can be present in the discontinuous phase include thickeners and viscosity modifiers. Suitable thickeners and viscosity modifiers include water-soluble polyacrylic and hydrophobically modified polyacrylic resins such as Carbopol and Pemulen, starches such as corn starch, potato starch, tapioca, gums such as guar gum, gum arabic, cellulose ethers such as hydroxypropyl cellulose, hydroxyethyl cellulose, carboxymethyl cellulose, and the like. These thickeners and viscosity modifiers will typically be included in a concentration in the range of from about 0.05 to about 0.5% of the discontinuous phase.

Other water soluble or dispersible materials that can be present in the discontinuous water phase include polycationic polymers to provide steric stabilization at the water-lipid interface and nonionic polymers that also stabilize the water-in-lipid-emulsion. Suitable polycationic polymers include RETEN 201, KYMENE 557H® and ACCO 7112. Suitable nonionic polymers include polyethylene glycols (PEG) such as CARBOWAX. These polycationic and nonionic polymers will typically be included in a concentration in the range of from about 0.1 to about 1.0% of the discontinuous phase.

Preferred embodiments of the present invention which contain skin care emulsions comprise an emulsifier capable of forming an emulsion of the discontinuous and continuous phases. In the emulsions of the present invention, the emulsifier is included in an effective amount. What constitutes an "effective amount" will depend on a number of factors including the respective amounts of the oil soluble agents, the type of emulsifier used, the level of impurities present in the emulsifier, and like factors. Typically, the emulsifier comprises from 0% to about 20%, preferably from about 0.01% to about 10%, and more preferably from about 0.1% to about 6% by weight of the skin care emulsion.

The emulsifiers useful in the present invention typically are oil soluble or miscible with the continuous phase materials, especially at the temperature at which the oil soluble material melts. It also should have a relatively low HLB value. Emulsifiers suitable for use in the present invention have HLB values typically in the range of from about 1 to about 7 and can include mixtures of different emulsifiers. Preferably, these emulsifiers will have HLB values from about 1.5 to about 6, and more preferably from about 2 to about 5.

A wide variety of emulsifiers are useful herein and include, but not limited to, those selected from the group consisting of sorbitan esters, glyceryl esters, polyglyceryl esters, methyl glucose esters, sucrose esters, ethoxylated fatty alcohols, hydrogenated castor oil ethoxylates, sorbitan ester ethoxylates, polymeric emulsifiers, and silicone emulsifiers.

Sorbitan esters are useful in the present invention. Preferable are sorbitan esters of C16–C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., ARLACEL® 83), sorbitan monoisostearate (e.g., CRILL® 6 made by Croda), sorbitan stearates (e.g., SPAN® 60), sorbitan triooleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Other suitable emulsifiers for use in the present invention include, but is not limited to, glyceryl monoesters, preferably glyceryl monoesters of C16–C22 saturated, unsaturated and branched chain fatty acids such as glyceryl oleate, glyceryl monostearate, glyceryl monopalmitate, glyceryl monobehenate, and mixtures thereof; polyglyceryl esters of C16–C22 saturated, unsaturated and branched chain fatty acids, such as polyglyceryl-4 isostearate, polyglyceryl-3 oleate, diglycerol monooleate, tetraglycerol monooleate and mixtures thereof; methyl glucose esters, preferably methyl glucose esters of C16–C22 saturated, unsaturated and branched chain fatty acids such as methyl glucose dioleate, methyl glucose sesquiisostearate, and mixtures thereof; sucrose fatty acid esters, preferably sucrose esters of C12–C22 saturated, unsaturated and branched chain fatty acids such as sucrose stearate, sucrose trilaurate, sucrose distearate (e.g., CRODESTA® F10), and mixtures thereof; C12–C22 ethoxylated fatty alcohols such as oleth-2, oleth-3, steareth-2, and mixtures thereof; hydrogenated castor oil ethoxylates such as PEG-7 hydrogenated castor oil; sorbitan ester ethoxylates such as PEG-40 sorbitan peroleate, Polysorbate-80, and mixtures thereof; polymeric emulsifiers such as ethoxylated dodecyl glycol copolymer; and silicone emulsifiers such as laurylmethicone copolyol, cetyldimethicone, dimethicone copolyol, and mixtures thereof In addition to these primary emulsifiers, the compositions of the present invention can optionally contain a coemulsifier to provide additional water-lipid emulsion stability. Suitable coemulsifiers include, but is not limited to, phosphatidyl cholines and phosphatidyl choline-containing compositions such as lecithins; long chain C16–C22 fatty acid salts such as sodium stearate; long chain C16–C22 dialiphatic, short chain C1–C4 dialiphatic quaternary ammonium salts such as ditallow dimethyl ammonium chloride and ditallow dimethyl ammonium methylsulfate; long chain C16–C22 dialkoyl(alkenoyl)-2-hydroxyethyl, short chain C1–C4 dialiphatic quaternary ammonium salts such as ditallowoyl-2-hydroxyethyl dimethyl ammonium chloride; the long chain C16–C22 dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate; short chain C1–C4 dialiphatic, long chain C16–C22 monoaliphatic benzyl quaternary ammonium salts such as dimethyl stearyl benzyl ammonium chloride, and synthetic phospholipids such as stearamidopropyl PG-dimonium chloride (PHOSPHOLIPID PTS from Mona Industries).

DEPOSITION AID

The articles of the present invention can further comprise from about 0.01% to about 10%, preferably from about 0.05% to about 7%, more preferably from about 0.10% to about 5%, and most preferably from about 0.15% to about 2%, based on the weight of the water insoluble substrate, of a deposition aid. Preferably, the deposition aid is water dispersable. By "water dispersible" is meant that the deposition aid is soluble in water at a concentration of 0.1% in water (distilled or equivalent) at 25° C., preferably at 0.5% concentration, more preferably at 1.0% concentration. Although optional, preferred embodiments of the present invention contain a deposition aid, especially if a water soluble skin care active is used.

Without being limited by theory, the deposition aid is believed to enhance deposition of the water soluble conditioning agents onto the skin or hair during the cleansing process, and also help the water soluble conditioning agent to adhere onto the surface of the skin and hair during the rinsing process. Generally, it is also believed that these deposition aids function, in part or in whole, via the following mechanisms: electrostatic attraction (mammalian skin is negatively charged); hydrophobic attraction because skin is more hydrophobic than water; and materials which are water dispersible in the presence of a surfactant but become water insoluble during the rinse process. One or more of the deposition aids useful herein can be added onto or impregnated into the substrate separately, or in combination with either the surfactant or the water soluble conditioning agents. The deposition aid can be cationic, nonionic, anionic, or zwitterionic, preferably cationic or nonionic, and more preferably cationic. Suitable deposition aids for use herein are described in U.S. Pat. Nos. 5,588,752, issued Nov. 18, 1997 to Turner et al., U.S. Pat. No. 5,624,666, issued Apr. 29, 1997 to Coffindaffer et al., U.S. Pat. No. 5,635,469, issued Jun. 3, 1997 to Fowler et al., U.S. Pat. No. 5,672,576, issued Sep. 30, 1997 to Behrens et al., U.S. Pat. No. 5,716,920, issued Feb. 10, 1998 to Glenn, Jr. et al., U.S. Pat. No. 5,720,964, issued Feb. 24, 1998 to Murray, and U.S. Pat. No. 5,714,446, issued Feb. 3, 1998 to Bartz et al., all of which references are incorporated herein in their entirety.

The *CTFA Cosmetic Ingredient Handbook*, Second Edition, 1992, which is incorporated by reference herein in its entirety, describes a wide variety of deposition aids which are suitable for use herein. Nonlimiting examples of useful deposition aids include cationic polymers, nonionic polymers, zeolites, clays and mixtures thereof. Cationic polymers are especially useful as deposition aids in the articles of the present invention, because they are believed to have the ability to associate with the negatively charged skin surface, thereby helping to keep the various components of the formulation upon the surface of the skin. Furthermore, cationic polymers are believed to form coascervates (e.g., water insoluble complexes) with the anionic surfactant.

The cationic polymers hereof will generally have a weight average molecular weight which is at least about 5,000, typically at least about 10,000, and is less than about 10 million. Preferably, the weight average molecular weight is from about 100,000 to about 5 million, more preferably about 200,000 to about 2 million. The cationic polymers will have cationic nitrogen-containing moieties such as quaternary ammonium or cationic amino moieties, or a mixture thereof. Suitable cationic polymers are described in U.S. Pat. Nos. 5,672,576, Behrens et al., issued Sep. 30, 1997, and 5,720,964, Murray, issued Feb. 24, 1998, both of which references are being incorporated herein be reference in their entirety.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

The cationic charge density is preferably at least about 0.3 meq/gram, more preferably at least about 0.6 meq/gram, even more preferably at least about 1.0 meq/gram, 1.2, most preferably at least about 1.2 meq/gram. The cationic charge density in general will be about 4 meq/gram or less, more generally about 3.0 meq/gram or less. Cationic charge density of the cationic polymer can be determined according to the Kjeldahl Method. Those skilled in the art will recognize that the charge density of amino-containing polymers in the final product may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., CI, Br, I, or F, preferably CI, Br, or I), sulfate, and methylsulfate. Others can also be used, as this list is not intended to be exhaustive.

As discussed above, the cationic polymer hereof is water dispersible. This does not mean, however, that it must become soluble when the articles of the present invention are wetted and agitated to produce lather. Preferably, however, the cationic polymer is either dispersible when the articles described herein are wetted and agitated to produce lather, or treat the water insoluble substrate with a pre-complexed coacervate phase formed by the cationic polymer and the anionic material. This complex coacervate phase can be added onto or impregnated into the substrate independently or in combination with either the lathering surfactant or the water soluble conditioning agent Complex coacervates of the cationic polymer can be formed with anionic surfactants or with anionic polymers that can optionally be added to the compositions hereof (e.g., sodium polystyrene sulfonate). Complex coacervates are believed to more readily deposit water soluble conditioning agents onto the skin or hair. Thus, in general, it is preferred that the cationic polymer exist in/on the articles of the present invention as a complexed coacervate phase or form a coacervate phase upon dilution of the lather produced after wetting and agitating these articles. If not already a coacervate in/on the articles of the present invention, the cationic polymer will preferably exist in a complex coacervate form upon dilution.

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature. Coacervate systems and the effect of these parameters has previously been studied. See, for example, J. Caelles, et al., "Anionic and Cationic Compounds in Mixed System", *Cosmetics Toiletries*, Vol, 106, April 1991, pp 49–54; Van Oss, "Coacervation, Complex-Coacervation and Flocculation", *J. Dispersion Science and Technology*, Vol. 9 (5,6), 1988–89, pp 561–573; D. J. Burgess, "Practical Analysis of Complex Coacervate Systems", *J. of Colloid and Interface Science*, Vol. 140, No. 1, November 1990, pp 227–238; and U.S. Pat. No. 5,716,920, Glenn Jr. et al., issued Feb. 10, 1998; all of which references being incorporated by reference herein.

Techniques for analysis of formation of complex coacervates are known in the art. For example, microscopic analyses of the lather, at any chosen stage of dilution, can be utilized to identify whether a coacervate phase has formed. Such coacervate phase will be identifiable as an additional emulsified phase. The use of dyes can aid in distinguishing the coacervate phase from other insoluble phases dispersed in the lather.

The nonionic and cationic polymers useful herein include those derived from both natural sources and synthetic sources. Among the polymers derived from natural sources, those that are derived from cellulose and proteins are highly preferred. Among the synthetic polymers, those that are polyethylenimines and polyacrylamides are preferred. General classes of suitable deposition aids for use in the articles described herein include gums, hydrophilic colloids and derivatives thereof, biological polymers and derivatives thereof, synthetic polymers, polymeric ethers, proteins and derivatives thereof, quaternary ammonium compounds, coacervates, and mixtures thereof The following are non-limiting examples of cationic and nonionic deposition aids for use herein.

Gums, hydrophilic colloids, biologica polymers, and proteins and mixtures thereof are useful herein as deposition aids. Nonlimiting examples of these materials include carboxymethyl hydroxyethylcellulose, carboxymethyl hydroxypropyl guar, carrageenan, cellulose gum, gelatin, guar gum, guar hydroxypropyltrimonium chloride, hydroxyethylcellulose, hydroxypropylcellulose, hydroxypropyl methylcellulose, methylcellulose, xanthan gum, chitin, chitosan, hydroxypropyl chitosan, potato starch, oat protein, milk protein, cocoyl hydrolyzed collagen, cocoyl hydrolyzed keratin, hydroxypropyltrimonium gelatin, and mixtures thereof.

Cellulose derived polymers are also useful herein as deposition aids. By cellulose derived polymers, as used herein, is meant to describe those polymers containing a cellulose backbone, i.e. a polysaccharide backbone of repeating glucose units. In these cellulose derived polymers, the hydroxy groups of the cellulose polymer have been hydroxyalkylated (preferably hydroxyethylated or hydroxypropylated) to form a hydroxyalkylated cellulose which is then further modified with a cationic quaternary ammonium or protonated ammonium group. Preferred cationic modifying groups are those having at least one $C_{10-20}$ alkyl chain and two shorter alkyl chains (i.e. $C_1$ or $C_2$) on the nitrogen. The substituent on the cellulose polymer can thus be depicted as —(X)NRR'R" wherein X is hydroxyalkyl (preferably—$OCH_2CH_2$— or —$OCH_2CHOHCH_2$—), R and R' are methyl or ethyl, and R" is $C_{10-20}$ alkyl [preferably lauryl, stearyl, or cocoyl (i.e. a mixture of alkyl groups derived from coconut oil)]. In other alternative structures it has been found that when R, R', and R" are all methyl (i.e. the trimonium group) that useful cellulose polymers are also obtained. In yet other alternative structures the cationic substituent on the cellulose contains both a hydroxyethyl and a hydroxypropyl group such that the moiety can be depicted as —($OCH_2CH_2O$)—$CH_2CHOHCH_2NRR'R"$ wherein R, R', and R" are methyl or ethyl, and R" is $C_{10-20}$ alkyl [preferably lauryl, stearyl, or cocoyl (i.e. a mixture of alkyl groups derived from coconut oil)], or alternatively wherein R, R', and R" are all methyl (i.e. the trimonium group).

Commercially available cationic modified celluloses include: laurdimonium hydroxethyl cellulose (wherein in the above formula X is —$OCH_2CH_2$—, R and R' are methyl, and R" is lauryl), steardimonium hydroxyethyl cellulose (wherein in the above formula X is —$OCH_2CH_2$—, R and R' are methyl, and R" is stearyl), and cocodimonium hydroxyethyl cellulose (wherein in the above formula X is —$OCH_2CH_2$—, R and R' are methyl, and R" is cocoyl). These three materials are known by the trade names Crodacel QL, Crodacel QS, and Crodacel QM, respectively, which are all commercially available from Croda Corp. Another highly useful cationic cellulose is laurdinmonium hydroxypropyl oxyethyl cellulose (wherein the modifying group on the cellulose is —($OCH_2CH_2O$)— $CH_2CHOHCH_2NRR'R"$, wherein R R' are methyl and R" is lauryl), which is commercially available as CRODACEL QL SPECIAL, from Croda Corp. Other useful cationic celluloses are available from Amerchol Corp. (Edison, N.J., USA) in their POLYMER JR$^{TN}$, LR$^{TN}$, and LK$^{TN}$ series of polymers, as salts of hydroxyethyl cellulose reacted with trimethyl ammonium substituted epoxide, referred to in the industry (CTFA) as Polyquatemium 10; cationic cellulose ethers described in U.S. Pat. Nos. 3,816,616 4,272,515, which are commercially available from Union Carbide Corp. under the trademark POLYMER JR.; and the polymeric quaternary ammonium salts of hydroxyethyl cellulose reacted with lauryl dimethyl ammonium-substituted epoxide, referred to in the industry (CTFA) as Polyquaternium 24 which are available from Amerchol Corp. (Edison, N.J., USA) under the tradename POLYMER LM-200.

Other suitable cationic polymers that can be used herein include cationic guar gum derivatives, such as the cationic polygalactomannan gum derivative described in U.S. Pat. No. 4,298,494 which are commercially available under the trademark JAGUAR; the hydroxypropyltrimethylammonium derivative of guar gum which is commercially available under the trademark JAGUAR C-13-S and JAGUAR C-17 (CTFA designation guar hydroxypropyltrimonium chloride); and the hydroxypropylated cationic guar derivative known as JAGUAR C-16 (commercially available from Celanese Corp. in their JAGUAR® series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein). Especially preferred cationic polymers include Polyquaternium 10.

Related to these cellulose polymers are ones having backbones that are derived from other sugars (or their related acids, alcohols, amines, etc.), e.g. galactose, mannose, arabinose, xylose, fucose, fructose, glucosamine, galactosamine, glucuronic acid, galacturonic acid, 5 or 6 membered ring polyalcohols, and mixtures thereof.

Protein derived Polymers are another type of useful derivative of a naturally occurring polymer. The protein derived polymers useful herein are derived from a wide variety of protein sources. However, those that are derived from hydrolyzed proteins (i.e. proteins which are broken down into lower molecular weight segments of from about 1000 MW to about 5000 MW) are preferred. Hydrolyzed proteins are well known to the cosmetic chemist of ordinary skill in the art and can be derived using standard synthetic techniques such as the acid, alkaline, or enzymatic hydrolysis of various protein sources. The protein source used will determine the ultimate amino acid composition of the hydrolyzed protein obtained. Nonlimiting examples of hydrolyzed proteins which are useful as polymers herein include those selected from the group consisting of hydrolyzed casein, hydrolyzed collagen, hydrolyzed conchiorin protein, hydrolyzed corn protein, hydrolyzed elastin, hydrolyzed fibronectin, hydrolyzed hair keratin, hydrolyzed human placental protein, hydrozlyed keratin, hydrolyzed potato protein, hydrolyzed rice protein, hydrolyzed silk, hydrolyzed soy protein, hydrolyzed vegetable protein, hydrolyzed wool protein, hydrolyzed wheat protein, and mixtures thereof. These hydrolyzed proteins are described in the CTFA International Cosmetic Ingredient Dictionary, 1991, pp. 246–249, which are incorporated by reference herein in their entirety.

It has been found that cationically modified hydrolyzed proteins are especially useful polymers in the present invention. Using a variety of synthetic techniques known to the artisan of ordinary skill in the chemical arts, the nitrogen atoms of the amino acids comprising these hydrolyzed proteins can be hydroxyalkylated (preferably hydroxyethylated or hydroxypropylated) to form a hydroxyalkylated protein hydrolyzate which is then further modified with a cationic quaternary ammonium or protonated ammonium group. Preferred cationic modifying groups are those having at least one $C_{10-20}$ alkyl chain and two shorter alkyl chains (i.e. $C_1$ or $C_2$) on the nitrogen. The substituent on the hydrolyzed protein can be depicted as —(X)NRR'R" wherein X is hydroxyalkyl (preferably—$OCH_2CH_2$— or —OCH$_2$CHOHCH$_2$—), R and R' are methyl or ethyl, and R" is C$_{10-20}$ alkyl [(preferably lauryl, stearyl, or cocoyl (i.e. a mixture of alkyl groups derived from coconut fats)]. In other alternative structures it has been found that when R, R', and R" are all methyl (i.e. the trimonium group) that useful cationic hydrolyzed proteins are also obtained. Commercially available cationic modified protein hydrolyzates include: hydroxypropyltrimonium hydrolyzed casein, hydroxypropyltrimoniurn hydrozlyed collagen, hydoxypropyltrimonium hydrolyzed keratin, hydroxypropyltrimonium hydrolyzed silk, hydroxypropyl trimonium hydrolyzed soy protein, hydroxypropyl trimonium hydrolyzed vegetable protein, and hydroxypropyltrimonium hydrolyzed wheat protein, wherein the —(X)NRR'R" substituent on each of these protein hydrolyzates is such that X is —OCH$_2$CHOHCH$_2$—, and R, R', and R" are methyl. These hydrolyzed proteins are described in the CTFA International Cosmetic Ingredient Dictionary, 1991, pp. 254–255, which are incorporated by reference herein in their entirety. Other commercially available cationic modified protein hydrolyzates include lauryldimonium hydroxypropyl hydrolyzed collagen, lauryldimonium hydroxypropyl hydrolyzed keratin, lauryldimonium hydroxypropyl hydrolyzed silk, lauryldimonium hydroxypropyl hydrolyzed soy protein, stearyldimonium hydroxypropyl hydrolyzed casein, stearyldimonium hydroxypropyl hydrolyzed collagen, stearyldimonium hydroxypropyl hydrolyzed keratin, stearyldimonium hydroxypropyl hydrolyzed rice protein, stearyldimonium hydorxypropyl hydrolyzed silk, stearyldimonium hydroxypropyl hydrolyzed vegetable protein, stearyldimonium hydroxypropyl hydrolyzed wheat protein, cocodimonium hydroxypropyl hydrolyzed casein, cocodimonium hydroxypropyl hydrolyzed collagen, cocodimonium hydroxypropyl hydrolyzed keratin, cocodimonium hydroxypropyl hydrolyzed rice protein, cocodimonium hydroxypropyl hydrolyzed silk, cocodimonium hydroxypropyl hydrolyzed soy protein, cocodimnoium hydroxypropyl hydrolyzed wheat protein, wherein in each of these protein hydrolyzates the —(X)NRR'R" substituent is such that X is —OCH2CHOHCH2—, R and R' are methyl, and R" is lauryl or stearyl or cocoyl. These hydrolyzed proteins are described in the CTFA International Cosmetic Ingredient Dictionary, 1991, pp. 112–113, 293–294, 586, which are incorporated by reference herein in their entirety. Preferred among these cationic hydrolyzed proteins are lauryldimmonium hydroxypropyl hydrolyzed collagen, lauryldimmonium hydroxypropyl hydrolyzed keratin, lauryldimmonium hydroxypropyl hydrolyzed keratin, lauryldimmonium hydroxypropyl hydrolyzed silk, lauryldimmonium hydroxypropyl hydrolyzed soy protein, and mixtures thereof.

Polymeric ethers are also useful as deposition aids herein as long as the number of repeating units is greater than 50. These materials are also known as polyethylene glycols and polypropylene glycols (designated as PEG and PPG in the CTFA, respectively). Nonlimiting examples of these materials include PEG 25M, PEG 75, PEG 90, PEG 100, PEG 2M, PEG 7M, PEG 14M, and mixtures thereof.

Synthetic polymers and copolymers are also useful as deposition aids herein. Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have C$_1$–C$_7$ alkyl groups, more preferably C$_1$–C$_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a C$_1$–C$_7$ alkyl, more preferably a C$_1$–C$_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium and quaternized pyrrolidone, e.g., alkyl vinyl imidazolium, alkyl vinyl pyridinium, alkyl vinyl pyrrolidone salts. The alkyl portions of these monomers are preferably lower alkyls such as the C$_1$–C$_3$ alkyls, more preferably C$_1$ and C$_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably C$_1$–C$_7$ hydrocarbyls, more preferably C$_1$–C$_3$, alkyls.

The cationic polymers hereof can comprise mixtures of monomer units derived from amine- and/or quaternary ammonium-substituted monomer and/or compatible spacer monomers.

Suitable synthetic cationic polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquatemium-16), such as those commercially available from BASF Wyandotte Corp. (Parsippany, N.J., USA) under the LUVIQUAT tradename (e.g., LUVIQUAT FC 370); copolymers of 1-vinyl-2-pyrrohdone and dimethylaminoethyl methacrylate (referred to in the industry by CTFA as Polyquaternium-11) such as those described in U.S. Pat. No. 4,080,310 and commercially available from ISP Corporation (Wayne, N.J., USA) under the GAFQUAT tradename (e.g., GAFQUAT 755 and 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; the mineral acid salts of amino-alkyl esters of homo- and co-polymers of unsaturated carboxylic acids having from 3 to 5 carbon atoms, as described in U.S. Pat. No. 4,009,256; the graft cationic copolymer containing N-vinylpyrrolidone, dimethylaminoethyl methacrylate and polyethylene glycol described in U.S. Pat. No. 4,048,301; the polymers of etherified starch described in U.S. Pat No. 3,186,911; cationic polyacrylamides of the type described in British Pat. App. 94031565.4; the high molecular weight cationic polymers designated in the CTFA as Quaternium-40 (a highly charged cationic dimethyldiallylammonium chloride homopolymer) and Quaternium-41 (a highly charged cationic copolymer prepared with dimethyldiallylammonium chloride and acrylamide), which are commercially available under the trademarks MERQUAT 100 and MERQUAT 550 from Merck & Corn., Inc.; and mixtures thereof. Further nonlimiting examples of other suitable synthetic polymers include acrylylates/C10-30 alkyl acrylate crosspolymer, acrylates copolymer, acrylates/PVP copolymer, acrylates/VA copolymer, butylated polyoxymethylene urea, butylated PVP, carbomer, hydroxyethyl PEI-1000, methyl methacrylate crosspolymer, PEI-1000, PEI-1500, PEI-2500, polybutene, polyacrylamide, polyacrylic acid, polyethylene, polyisobutene, polymethyl methacrylate, polystyrene, polyvinyl alcohol, PVP, PVP/Eicosene copolymer, PVP/VA copolymer, sodium acrylates copolymer, sodium carbomer, sodium polyacrylate, sodium polymethacrylate, styrene/PVP copolymer, TEA carbomer, and mixtures thereof.

Other polymers: Other useful polymers include polyvinylpyrrolidone and copolymers of vinylpyrrolidone such as those containing vinyl acetate, dimethylaminoethylmethacrylate and quaternary versions of the same with methyl sulfates, and polymers and copolymers of vinyl alcohol and vinyl acetate. Another highly useful polymer is the protonated form of polyethyleneimine. Polyethylenimine is a polymer which is produced from the polymerization of ethylenimine. The protonated polyethylenimine polymers preferred herein are those having a molecular weight of from about 500,000 to about 750,000, branching such that the ratio of primary to secondary to tertiary nitrogen is about 1:2:1, a tertiary nitrogen site on average at about every 3 to about 3.5 atoms, a charge density of about 20 milliequivalents per gram at pH 4.5, a density of about 1070 kg/m$^3$, and a viscosity of about 17,000 to about 28,000 milli-Pascals. A protonated polyethylenimine polymer meeting this description is commercially available as POLYMIN P from BASF Corp.

Cationic surfactants (nonpolymeric) are also useful herein as deposition aids herein, provided that these materials are selected so as to not interfere with the overall lathering characteristics of the required lathering surfactants. Cationic surfactants useful herein contain amino or quaternary ammonium hydrophilic moieties which are positively charged when dissolved in the aqueous composition of the present invention. Cationic surfactants suitable for use are disclosed in the following documents, all incorporated by reference herein: M.C. Publishing Co., *McCutcheon's, Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; U.S. Pat No. 4,275,055, Nachtigal, et al., issued Jun. 23, 1981; U.S. Pat. No. 4,387,090, Bolich, Jr., issued Jun. 7,.1983; U.S. Pat. No. 4,704,272, Oh et al, issued Nov. 3, 1987; U.S. Pat. No. 5,034,218, Duvel, issued Jul. 23, 1991; U.S. Pat. No. 5,393,452, Raleigh et al, issued Sep. 14, 1993; U.S. Pat. No. 5,672,576, Behrens et al., issued Sep. 30, 1997; U.S. Pat. No. 5,714,446, Bartz et al., issued Feb. 3, 1998.

Among the quaternary ammonium-containing cationic surfactant materials useful herein are those of the general formula:

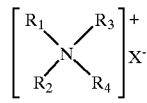

wherein $R_1$–$R_4$ are independently selected from hydrogen, an aliphatic group of from about 1 to about 22 carbon atoms, or aromatic, aryl, an alkoxy, polyoxyalkylene, alkylamido, hydroxyalkyl, or alkylaryl group having from about 1 to about 22 carbon atoms; and X is an anion selected from halogen, acetate, phosphate, nitrate, sulfate, alkylsulfate radicals (e.g., methyl sulfate and ethyl sulfate), tosylate, lactate, citrate, and glycolate. The aliphatic groups may contain, in addition to carbon and hydrogen atoms, ether linkages, and other groups such as hydroxy or amino group substituents (e.g., the alkyl groups can contain polyethylene glycol and polypropylene glycol moieties). The longer chain aliphatic groups, e.g., those of about 12 carbons, or higher, can be saturated or unsaturated.

More preferably, $R_1$ is an alkyl group having from about 12 to about 18 carbon atoms; $R_2$ is selected from H or an alkyl group having from about 1 to about 18 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 18 carbon atoms; $R_2$, $R_3$, and $R_4$ are selected from H or an alkyl group having from about 1 to about 3 carbon atoms; and X is as described previously.

Alternatively, other useful cationic surfactants include amino-amides, wherein in the above structure $R_1$ is alternatively $R_5CO$—$(CH_2)_n$—, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, steararnidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Preferred cationic surfactants useful herein include those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

Among the cationic polymers useful herein, preferred are those selected from the group consisting of hydroxyethyl cellulose, hydroxypropyl cellulose, lauryldimmonium hydroxypropyl oxyethyl cellulose, laurdimonium hydroxyethyl cellulose, steardimonium hydroxyethyl cellullose, cocodimonium hydroxyethyl cellulose, hydroxypropyl hydrolyzed collagen, lauryldimmonium hydroxypropyl hydrolyzed keratin, lauryldimmonium hydroxypropyl hydrolyzed keratin, lauryldimmonium hydroxypropyl hydrolyzed silk, lauryldimmonium hydroxypropyl hydrolyzed soy protein, protonated polyethylenimine, Polyquaternium 10, and mixtures thereof. More preferred are lauryldimonium hydroxypropyl hydrolyzed collagen, laurdimonium hydroxypropyl oxyethyl cellulose, and mixtures thereof. Preferably the deposition aid is selected from the group comprising hydroxyalkyl cellulose ethers and cationic guar derivatives. Particularly preferred deposition aids are JAGUAR C13S with a cationic charge density of 0.8 meq/g. Other particularly preferred materials include JAGUAR C15, JAGUAR C17, JAGUAR C16, JAGUAR C162, Polyquaternium 10, and mixtures thereof. Most preferred is Polyquatemium 10 (e.g., POLYMER JR400 and POLYMER JR30M).

Among the nonionic polymers useful herein, preferred are those selected from the group consisting of hydrolyzed casein, hydrolyzed collagen, hydrolyzed vegetable protein, guar gum, polyvinylpyrrolidone, PEG 14M, and mixtures thereof. More preferred is PEG 14M and hydrolyzed casein.

WEIGHT RATIOS AND WEIGHT PERCENTAGES

In the present invention, the weight ratio of the lathering surfactant to the skin care active is from about 1000:1 to about 1:1, preferably from about 800:1 to about 2:1, and more preferably from about 500:1 to 3:1.

ADDITIONAL INGREDIENTS

The articles of the present invention can comprise a wide range of optional ingredients. Some of these ingredients are listed in more detail herein. Particularly useful are various active ingredients useful for delivering various conditioning benefits during the cleansing process. In these compositions, the article is useful for also delivering these conditioning ingredients to the skin or hair.

Conditioning Component

The articles of the present invention can optionally comprise a conditioning component which is useful for providing a conditioning benefit to the skin or hair during the use of the article. By "conditioning benefit," as used herein, describes the ability of a material (e.g., compound or composition), in whole or in part, to improve the appearance and/or feel of mammalian skin upon/after topical application (e.g., after rinsing and pat drying) via one or more of the following mechanisms: moisturization, hydration, plasticization, lubrication, and occlusion. Nonlimiting examples of materials which suitably perform these mechanisms are described in the *CTFA Cosmetic Ingredient Handbook*, Second Edition, 1992, which is incorporated by reference herein in its entirety. The articles of the present invention comprise from about 0.05% to about 99%, preferably from about 0.1% to about 50%, and more preferably from about 1% to about 25% of a conditioning component, by weight of said water insoluble substrate.

The conditioning component of the present invention can comprise: a water soluble conditioning agent; an oil soluble conditioning agent; a conditioning emulsion; or any combination or permutation of the three. By conditioning emulsion is meant that conditioning agents are present in the skin care emulsions described hereinbefore, e.g., in either the water soluble discontinuous phase or the oil soluble continuous phase. The oil soluble conditioning agent is selected from one or more oil soluble conditioning agents such that the weighted arithmetic mean solubility parameter of the oil soluble conditioning agent is less than or equal to 10.5. The water soluble conditioning agent is selected from one or more water soluble conditioning agents such that the weighted arithmetic mean solubility parameter of the water soluble conditioning agent is greater than 10.5. It is recognized, based on this mathematical definition of solubility parameters, that it is possible, for example, to achieve the required weighted arithmetic mean solubility parameter, i.e. less than or equal to 10.5, for an oil soluble conditioning agent comprising two or more compounds if one of the compounds has an individual solubility parameter greater than 10.5. Conversely, it is possible to achieve the appropriate weighted arithmetic mean solubility parameter, i.e. greater than 10.5, for a water soluble conditioning agent comprising two or more compounds if one of the compounds has an individual solubility parameter less than or equal to 10.5. The solubility parameters of conditioning agents can be determined as described hereinbefore in the Skin Care Active Component Section.

Nonlimiting examples of conditioning agents useful as oil soluble conditioning agents include those selected from the group consisting of mineral oil, petrolatum, C7–C40 branched chain hydrocarbons, C1–C30 alcohol esters of C1–C30 carboxylic acids, C1-C30 alcohol esters of C2–C30 dicarboxylic acids, monoglycerides of C1–C30 carboxylic acids, diglycerides of C1-C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol C4–C20 alkyl ethers, di C8–C30 alkyl ethers, and mixtures thereof.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, *Drug. Cosmet. Ind.*, 89, 36–37, 76, 78–80, 82 (1961); and International Cosmetic Ingredient Dictionary, Fifth Edition, vol. 1, p. 537 (1993), which are incorporated by reference herein in their entirety.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the C7–C40 isoparaffins, which are C7–C40 branched hydrocarbons.

Also useful are C1–C30 alcohol esters of C1–C30 carboxylic acids and of C2–C30 dicarboxylic acids, including straight and branched chain materials as well as aromatic derivatives. Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, cetyl ricinoleate, cholesterol hydroxystearate, cholesterol isostearate, and mixtures thereof.

Also useful are various C1–C30 monoesters and polyesters of glycerin and related materials. These esters are derived from glycerin and one or more carboxylic acid moieties. Depending on the constituent acid and glycerin, these esters can be in either liquid or solid form at room temperature. Nonlimiting examples of solid esters include: glyceryl tribehenate, glyceryl stearate, glyceryl palmitate, glyceryl distearate, glyceryl dipalmitate.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Lefton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991, which is incorporated by reference herein in its entirety. The polyalkylsiloxanes correspond to the general chemical formula $R_3SiO[R_2SiO]_xSiR_3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonlimiting examples of which include the VICASIL® series sold by General Electric Company and the DOW CORNING® 200 series sold by Dow Corning Corporation. Specific examples of polydimethylsiloxanes useful herein include DOW CORNING® 225 fluid having a viscosity of 10 centistokes and a boiling point greater than 200° C., and DOW CORNING® 200 fluids having viscosities of 50, 350, and 12,500 centistokes, respectively, and boiling points greater than 200° C. Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and integer from about 1 to about 500. A commercially available trimethylsiloxysilicate is sold as a mixture with dimethicone as DOW CORNING® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. DOW CORNING® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 METHYLPHENYL FLUID (sold by General Electric Company) and 556 COSMETIC GRADE PHENYL TRIMETHICONE FLUID (sold by Dow Corning Corporation).

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, dioctyl ether, dodecyl octyl ether, and mixtures thereof.

Other useful oil soluble conditioning agents include CREMEROL (available from Amerchol), ELDEW CL301 (available from Ajinomoto), MODULAN (an acetylated lanolin which is commercially available from Croda), OHLAN (a hydroxylated lanolin which is commercially available from Amerchol), phytantriol, super sterol esters, such as $C_1$–$C_{30}$ cholesteroltlanosterol esters, (available from Croda), and mixtures thereof.

Nonlimiting examples of conditioning agents useful as water soluble conditioning agents include those selected from the group consisting of polyhydric alcohols, polypropylene glycols, polyethylene glycols, ureas, pyrolidone carboxylic acids, ethoxylated and/or propoxylated C3–C6 diols and triols, alpha-hydroxy C2–C6 carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful water soluble conditioning agents include materials such as urea; guanidine; glycolic acid and glycolate salts (e.g. ammonium and quaternary alkyl ammonium); lactic acid and lactate salts (e.g. ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-4, PEG-5, PEG-6, PEG-8, PEG-9, PEG-10, PEG-15 PEG-30, PEG-50, polypropylene glycols such as PPG-9, PPG-12, PPG-15, PPG-17, PPG-20, PPG-26, PPG-30, PPG-34; alkoxylated glucose; hyaluronic acid; and mixtures thereof. Also useful are materials such as aloe vera in any of its variety of forms (e.g., aloe vera gel), chitin, starch-grafted sodium polyacrylates such as SANWET (RTM) IM-1000, IM-1500, and IM-2500 (available from Celanese Superabsorbent Materials, Portsmouth, Va.); lactamide monoethanolamine; acetamide monoethanolamine; and mixtures thereof. Also useful are propoxylated glycerols as described in propoxylated glycerols described in U.S. Pat. No. 4,976,953, to Orr et al., issued Dec. 11, 1990, which is incorporated by reference herein in its entirety. Other useful water soluble conditioning agents include arginine, arginine asparate (available from Ajinomoto), ARGININE PCA (available from Argidone-UCIB), 1,3 butylene glycol, CHITOLAM NB/101 (available from Lamberti), chitosan salts, Codiavelane (available from Secma), COLLAGEN AMINO ACID (available from Crotein CAA-Croda), creatine, dextran, dextrin, diglycerol, dipropylane glycol, ectoines, erythritol, FUCOGEL (available from Solabia), fructose, glucamine salts, glucose glutamate (commercially available as WICKENOL 545 from Caschem), glucuronic acid salts, glutamic acid salts, glycereth 12, glycereth 20, glycereth 7, glycerin, glyceryl PCA, glycogen, hexylene glycol, honey, hyaluronic acid, hydrogenated honey, hydrogenated starch hydrolysates, hydrolyzed mucopolysaccharides, hydroxy proline, Indinyl CA (available from Laboratoires Serobiologiques), inositol, keratin amino acids (commercially available as CROTEIN HKP from Croda), konjac mannan, Larex A-200 (available from Larex), LYSINE PLA (commercially available as LYSIDONE from UCIB), maltitol, maltose, mannitol, mannose, Mariscan (available from Pentapharm), Melhydrin (available from Laborotories Serobiologiques), methoxy PEG 10, methoxy, methyl gluceth 10 (commercially available as GLUCAM E10 from Amerchol), methyl gluceth 20 (commercially available as GLUCAM E20 from Amerchol), methyl glucose, 3 methyl 1,3 butandiol, N acetyl glucosamine salts, panthenol, PEG 15 butanediol, butanediol, PEG 5 pentaerythitol, pentaerythitol, Pentaglycan (available from Pentapharm), 1,2 pentanediol, phytohyaluron (jute extract), polyglycerol sorbitol, PPG 1 glyceryl ether, proline, propylene glycol, 2 pyrrolidone-5-carboxylic acid and its salts, saccharide isomerate (commercially available as PENTAVITIN from Pentapharm), Seacare (available from Secma), Sericin (available from Pentapharm), serine, silk amino acids (commercially available as CROSLIK LIQUID from Croda), sodium acetylhyaluronate, sodium hyaluronate, sodium polyaspartate (commercially available as AQUADEW SPA-30 from Ajinomoto), sodium polyglutamate (commercially available as AJICOAT SPG from Ajinomoto), sorbeth 20, sorbeth 6, sorbitol, trehalose, triglycerol, trimethyolpropane, tris (hydroxymethyl) amino methane salts, xylitol, xylose, and mixtures thereof.

HARDNESS VALUE

In embodiments further comprising a conditioning component comprising an oil soluble conditioning agent, the skin care active component will preferably have a minimum hardness value about 0.02 kg. The hardness value is a physical hardness measurement of the combination of all ingredients (e.g., water soluble skin care actives, oil soluble skin care actives, and conditioning agents) within the skin care active component. It is believed that increasing the hardness value increases deposition consistency of the skin care actives and conditioning agents despite variations in lathering techniques employed by the consumer. It is believed that increasing skin care active component hardness decreases transfer within the substrate and also decreases emulsification of the skin care active component by the surfactants during the lathering step. As a result, more of the skin care active component remain available for mechanical transfer via contact with the skin or hair.

The skin care active component of the present invention has a hardness value of greater than about 0.02 kg, preferably greater than about 0.05, and more preferably greater than about 0.10. Preferably, the hardness value of the skin care active component should not be greater than about 5.00 kg., more preferably about 4.00 kg, most preferably 3.00, because hardness levels beyond this point can negatively affect deposition of the ingredients in the skin care active component to the skin or hair.

Hardness Test

The hardness value is measured by a test traditionally used to measure bar soap hardness. A Chatillon force gauge is employed to measure the hardness value of a 5–8 oz. sample of the skin care active component. Several readings are taken, each on a fresh sample, to obtain an average value. The Chatillon force gauge model no. DFIS100 is manufactured by Chatillon Corporation which is located in Greensboro, N.C.

Materials Used to Increase Hardness Value

The cleansing articles of the present invention may comprise a hardening material used in combination with the skin care actives comprising the skin care active component described hereinbefore. Many materials can be used as both a conditioning agent and as a lipid hardening material. In fact, any solid conditioning agent, described hereinbefore, may be used as a hardening material. The amount of the hardening material needed to achieve the minimum hardness value of 0.02 kg. is dependent upon the particular material used and can be easily determined by one of ordinary skill in the art The hardening material can be used as an individual hardening material or a combination of hardening materials, and is included at concentrations ranging from about 0.1% to about 99.9%, preferably from about 0.5% to about 75%, more preferably from about 1% to about 50%, even more preferably from about 2% to about 25%, by weight of the skin care active component.

As used herein the term "hardening materials" refers to those materials which have a melting point above about 30° C., preferably above about 30° C. to about 250° C., more preferably from about 37° C. to about 100° C., even more preferably from about 37° C. to about 80° C.

Any material may be used to increase the hardness value of the skin care active component provided that the following criteria are met: (i) the material must be soluble in the skin care actives of the skin care active component and (ii) the material must have a melting point of greater than 20° C. (e.g., be a solid at room temperature). Examples of suitable hardening materials include, but are not limited to, petrolatum, highly branched hydrocarbons, fatty alcohols, fatty acid esters, vegetable oils, hydrogenated vegetable oils, polypropylene glycols, alpha-hydroxy fatty acids, fatty acids having from about 10 to about 40 carbon atoms, alkyl amides of di and/or tri-basic carboxylic acids, n-acyl amino acid derivatives, and mixtures thereof. Hardening materials useful in the present invention are further described in U.S. Pat. No. 4,919,934, to Deckner et al., issued Apr. 24 1990, which is incorporated herein by reference in its entirety.

Suitable highly branched hydrocarbons for use herein include hydrocarbon compounds having from about 17 to about 40 carbon atoms. Nonlimiting examples of these hydrocarbon compounds include squalane, cholesterol, lanolin, docosane (i.e. a $C_{22}$ hydrocarbon), and isoparaffins.

Suitable fatty alcohols for use herein include monohydric alcohols, ethoxylated fatty alcohols, and fatty alcohol esters, excluding the ethoxylated fatty alcohols and fatty alcohol esters useful as emulsifiers herein. Specific examples of commercially available fatty alcohols include, but are not limited to, UNILIN 550, UNILIN 700, UNILIN 425, UNILIN 400, UNILIN 350, AND UNILIN 325, all of which are available from Petrolite. Suitable ethoxylated fatty alcohols include, but are not limited, UNITHOX 325, UNITHOX 400, AND UNITHOX 450, UNITHOX 480, UNITHOX 520, UNITHOX 550, UNITHOX 720, UNITHOX 750, all of which are available from Petrolite. Non-limiting examples of suitable esters of fatty alcohols include tri-isostearyl citrate, ethyleneglycol di-12-hydroxystearate, tristearylcitrate, stearyl octanoate, stearyl heptanoate, trilaurylcitrate.

Suitable fatty acid esters for use herein include ester waxes, monoglycerides, diglycerides, triglycerides and mixtures thereof. Non-limiting examples of suitable ester waxes include stearyl stearate, stearyl behenate, palmityl stearate, stearyl octyldodecanol, cetyl esters, cetearyl behenate, behenyl behenate, ethylene glycol distearate, ethylene glycol dipalmitate, and beeswax. Examples of commercial ester waxes include KESTER waxes from Koster Keunen, CRODAMOL SS from Croda and DEMALCARE SPS from Rhone Poulenc.

Vegetable oils and hydrogenated vegetable oils which are solid or semi-solid at ambient temperatures of from about 20° C. to about 25° C. are also useful herein as hardening materials. Examples of suitable vegetable oils and hydrogenated vegetable oils include butterfat, chicken fat, goose fat, horse fat, lard (fatty tissue) oil, rabbit fat, sardine oil, tallow (beef), tallow (mutton), chinese vegetable tallow, babassu oil, cocoa butter, coconut oil, palm oil, palm kernal oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, derivatives thereof and mixtures thereof.

Examples of suitable alpha-hydroxy fatty acids and fatty acids having from about 10 to about 40 carbon atoms include 12-hydroxystearic acid, 12-hydroxylauric acid, 16-hydroxyhexadecanoic acid, behenic acid, eurcic acid, stearic acid, caprylic acid, lauric acid, isostearic acid, and mixtures thereof Examples of some suitable fatty acids are further described in U.S. Pat. No. 5,429,816, issued to Hofrichter et al. on Jul. 4, 1995; and U.S. Pat. No. 5,552,136, issued to Motley on Sep. 3, 1996, which descriptions are incorporated herein by reference.

Suitable alkyl amides of di and/or tri-basic carboxylic acids for use herein include disubstituted or branched monoamides, monosubstituted or branched diamides, triamides, and mixtures thereof. Some specific examples of alkyl amides of di- and tri-basic carboxylic acids include, but are not limited to, alkyl amides of citric acid, tricarballylic acid, aconitic acid, nitrilotriacetic acid and itaconic acid such as 1,2,3-propane tributylamide, 2-hydroxy-1,2,3-propane tributylamide, 1-propene-1,2,3-trioctylamide, N,N', N"-tri(methyldecylamide)amine, 2 docecyl-N,N'-dibutylsuccinamide, and mixtures thereof. Other suitable amides include the n-acyl amino acid derivatives described in U.S. Pat. No. 5,429,816, issued to Hofrichter et al. on Jul. 4, 1995.

Also suitable for use in the present invention are waxes having a HLB of from about 1 to about 10, preferably from about 6 and most preferably from about 5. The HLB (short for "Hydrophile-Lipophile Balance") value system is fully described, and values for various materials are provided, in the publication *The Time-Saving Guide to Emulsifier Selection* (published by ICI Americas Inc., Wilmington, Del.; 1984), the disclosure of which are incorporated herein by reference in their entirety.

Useful ester waxes include $C_{10}$–$C_{40}$ fatty acid, diesters, of $C_{10}$–$C_{40}$ fatty acids where the alcohol is propylene glycol, ethylene glycol, polyethylene glycol, polypropylene glycol, polyglycerin, or glycerin, triglycerides or diglycerides of $C_{10}$–$C_{40}$ fatty acids, pentaerythritol tri- ortetra-esters of $C_{10}$–$C_{40}$ fatty acids, $C_{10}$–$C_{40}$ fatty acids of sorbitan triesters, $C_{10}$–$C_{40}$ fatty acids of sucrose polyesters having 3–8 moles of substitution, myristyl myristate, paraffin, synthetic waxes such as Fischer-Tropsche waxes, microcrystalline waxes, castor wax, partially hydrogenated vegetable oils, behenyl behenrate and myristyl propionate and mixtures thereof.

Useful diester waxes include SYNCHROWAX ERL-C (C18-36 acid glycolester) (available from Croda) and propylene glycol diester waxes including ethylene glycol distearate and glycol distearate. Useful triglyceride waxes include shea butter, cocoa butter, SYNCHROWAX HGL-C (C18-36 acid triglyceride), SYNCHROWAX HRC (tribehenin), SYNCHROWAX HRS-C [tribehenin (and) calcium behenate] (all available from Croda Inc.), tristearin, trimyristate and fully hydrogenated vegetable oils and mixtures thereof. Preferred is a mixture of diester and triglyceride waxes in a ratio of from about 5:1 to about 1:1 and more preferably from about 4:1 to about 1:1.

Waxes useful in the compositions of this invention are disclosed in the following, all of which are incorporated by reference herein in their entirety: U.S. Pat No. 5,219,558 to Woodin, Jr. et al., issued Jun. 15, 1993; U.S. Pat. No. 4,049,792, to Elsnau, issued Sept. 20, 1977; U.S. Pat. No. 4,151,272, to Geary et al., issued Apr. 24, 1975; U.S. Pat. No. 4,229,432, to Geria, issued Oct. 21, 1980; U.S. Pat No. 4,280,994, to Turney, issued Jul. 28, 1981; U.S. Pat. No. 4,126,679, to Davy et al., issued Nov. 21, 1978; and European Pat. Application Publication Number 117,070 to May, published Aug. 29, 1984, "The Chemistry and Technology of Waxes", A. H. Warth, 2nd Edition, reprinted in 1960, Reinhold Publishing Corporation, pp. 391–393 and 421; "The Petroleum Chemicals Industry", R. F. Goldstein and A. L. Waddeam, 3rd Edition (1967), E & F.N. Span Ltd., pp. 33–40; "The Chemistry and Manufacture of Cosmetics", M. G. DeNavarre, 2nd Edition (1970), Van Nostrand & Company, pp. 354–376; and in "Encyclopedia of Chemical Technology:, Vol. 24, Kirk-Othmer, 3rd Edition (1979) pp. 466–481.

Additional non-limiting examples of useful hardening materials are those selected from the group consisting of sorbitan esters, glyceryl esters, polyglyceryl esters, methyl glucose esters, sucrose esters, ethoxylated fatty alcohols, hydrogenated castor oil ethoxylates, sorbitan ester ethoxylates, polymeric emulsifiers, and silicone emulsifiers.

Sorbitan esters are useful in the present invention. Preferable are sorbitan esters of C16–C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., ARLACEL® 83), sorbitan monoisostearate (e.g., CRILL® 6 made by Croda), sorbitan stearates (e.g., SPAN® 60), sorbitan triooleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Other suitable hardeners for use in the present invention include, but is not limited to, glyceryl monoesters, preferably glyceryl monoesters of C16–C22 saturated, unsaturated and branched chain fatty acids such as glyceryl oleate, glyceryl monostearate, glyceryl monopalmitate, glyceryl monobehenate, and mixtures thereof; polyglyceryl esters of C16–C22 saturated, unsaturated and branched chain fatty acids, such as polyglyceryl-4 isostearate, polyglyceryl-3 oleate, diglycerol monooleate, tetraglycerol monooleate and mixtures thereof; methyl glucose esters, preferably methyl glucose esters of C16–C22 saturated, unsaturated and branched chain fatty acids such as methyl glucose dioleate, methyl glucose sesquiisostearate, and mixtures thereof; sucrose fatty acid esters, preferably sucrose esters of C12–C22 saturated, unsaturated and branched chain fatty acids such as sucrose stearate, sucrose trilaurate, sucrose distearate (e.g., CRODESTA® F10), and mixtures thereof; C12–C22 ethoxylated fatty alcohols such as oleth-2, oleth-3, steareth-2, a mixtures thereof; hydrogenated castor oil ethoxylates such as PEG-7 hydrogenated castor oil; sorbitan ester ethoxylates such as PEG-40 sorbitan peroleate, polysorbate-80, and mixtures thereof; polymeric emulsifiers such as ethoxylated dodecyl glycol copolymer; and silicone emulsifiers such as laurylmethicone copolyol, cetyldimethicone, dimethicone copolyol, and mixtures thereof.

Other useful hardeners include, but are not limited to, phosphatidyl cholines and phosphatidyl choline-containing compositions such as lecithins; long chain C16–C22 fatty acid salts such as sodium stearate; long chain C16–C22 dialiphatic, short chain C1–C4 dialiphatic quaternary ammonium salts such as ditallow dimethyl ammonium chloride and ditallow dimethyl ammonium methylsulfate; long chain C16–C22 dialkoyl(alkenoyl)-2-hydroxyethyl, short chain C1–C4 dialiphatic quaternary ammonium salts such as ditallowoyl-2-hydroxyethyl dimethyl ammonium chloride; the long chain C16–C22 dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate; short chain C1–C4 dialiphatic, long chain C16–C22 monoaliphatic benzyl quaternary ammonium salts such as dimethyl stearyl benzyl ammonium chloride, and synthetic phospholipids such as stearamidopropyl PG-dimonium chloride (PHOSPHOLIPID PTS from Mona Industries).

Other Optional Ingredients

The compositions of the present invention can comprise a wide range of other optional components. These additional components should be pharmaceutically acceptable. The *CTFA Cosmetic Ingredient Handbook*, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these and other functional classes include: abrasives, absorbents, anticaking agents, antioxidants, vitamins, binders, biological additives, buffering agents, bulking agents, chelating agents, chemical additives, colorants, cosmetic astringents, denaturants, drug astringents, film formers, fragrance components, opacifying agents, pH adjusters, preservatives, propellants, and reducing agents.

Also useful herein are aesthetic components such as fragrances, pigments, colorings, essential oils, skin sensates, and astringents.

METHODS OF MANUFACTURE

The disposable, single use personal care cleansing articles of the present invention are manufactured by separately or simultaneously adding onto or impregnating into the water insoluble substrate (e.g., in any permutation) a lathering surfactant, a skin care active component, and preferably a deposition aid. The optional conditioning component can also be separately or simultaneously added onto or impregnated into the substrate with the other three components. By "separately" is meant that the surfactants and the skin care active component can be added sequentially, in any order without first being combined together. By "simultaneously" is meant that the surfactants and conditioning agents can be added at the same time, with or without first being combined together.

Preferably, the lathering surfactant and the skin care active component are added separately to prevent emulsification of the skin care actives. This separate treatment of the substrate also applies to the optional conditioning component. In this preferred embodiment, the optional deposition aid can be (i) mixed with the lathering surfactant before treating the substrate with such a mixture, (ii) mixed with the skin care active component before treating the substrate with such a mixture, or (iii) separately added onto or impregnated into the substrate. However, if the surfactant is added via a dip/nip process, it is preferred to added the skin care active component and any optional components to the substrate after application of the surfactant. Despite the order of treatment excess surfactant, skin care active component, and/or deposition aid should be removed (e.g., by a nipping process). Thereafter, the treated substrate should be dried by conventional means. The surfactant, skin care component, deposition aid, and any optional ingredients can be added onto or impregnated into the substrate by any means known to those skilled in the art: for example, by spraying, laser printing, splashing, dipping, soaking, or coating (e.g., extrusion coating and slot coating).

When water or moisture is used or present in the manufacturing process, the resulting treated substrate is then dried so that it is substantially free of water. The treated substrate can be dried by any means known to those skilled in the art. Nonlimiting examples of known drying means include the use of convection ovens, radiant heat sources, microwave ovens, forced air ovens, and heated rollers or cans. Drying also includes air drying without the addition of heat energy, other than that present in the ambient environment. Also, a combination of various drying methods can be used.

METHODS OF MAINTAINING THE SKIN CARE ACTIVES SUBSTANTIALLY ON THE SURFACE OF THE SUBSTRATE

The products of the present invention effectively and efficiently deliver skin care actives to the skin and hair by maintaining the skin care actives substantially on the surface of the substrate. The following subsections discuss in further detail the processes and compositional improvements which allow a Surface to Saturation Ratio of greater than or equal to about 1.25. All of the following processing and compositional improvements can be used individually or in combination to maintain the skin care actives substantially on the surface. The term "chemical component," as used herein, means the skin care active or a combination of the conditioning agent and the skin care active.

Chemical Treatment of the Substrate

One method of substantially maintaining the chemical component on the surface of the substrate is by chemically treating the substrate or the fibers of the substrate with either a hydrophobic or hydrophilic substance. Choosing the appropriate substance (hydrophobic or hydrophilic) is dependent on the chemical component that is meant to be deposited. For example, if a oil soluble conditioning agent is to be deposited onto the skin or hair, the substrate or its fibers would typically be treated with a hydrophilic substance, and vice versa. Because most substrates are hydrophobic by their nature, e.g., usually derived from polyolefins, this section will concentrate on hydrophilic chemical treatment of the substrate.

Any of a wide variety of surfactants, including ionic and nonionic surfactants, may be employed to hydrophilically modify the substrate. Suitable surfactants may be internal modifiers, e.g., the modifying compounds are added to the polymer composition prior to spinning or forming fibers, or topical modifiers, e.g., the modifying compounds are topically applied during or subsequent to the formation of fibers or nonwoven webs. An internal modification process is disclosed in U.S. Pat. No. 4,578,414 to Sawyer et al, and a topical modification process is disclosed in U.S. Pat. No. 5,057,361 to Sayovitz et al., both references incorporated herein in their entirety.

Nonlimiting examples of suitable surfactants include silicone based surfactants, e.g., polyalkeleneoxide modified polydimethyl siloxane; fluoroaliphatic surfactants, e.g., perfluoroalkyl polyalkylene oxides; and other surfactants, e.g., actyl-phenoxypolyethoxy ethanol nonionic surfactants, alkylaryl polyether alcohols, and polyethylene oxides. Commercially available surfactants suitable for the present invention include various poly(ethylene oxide) based surfactants available under the tradename TRITON, e.g., grade X-102, from Rohm and Haas Corp.; various polyethylene glycol based surfactants available under the tradename EMEREST, e.g., grades 2620 and 2650, from Emery Indust.; various polyalkylene oxide modified polydimethylsiloxane based surfactants available under the tradename SILWET, e.g., grade Y12488, from OSI Specialty Chemicals; and alkenyl succinamide surfactants available under the tradename LUBRIZOL, e.g., grade OS85870, from Lubrizol Corp.; and polyoxyalkylene modified fluoroaliphatic surfactants available from Minnesota Mining and Manufacturing Co. The amount of surfactants required and the hydrophilicity of the modified substrate or fibers of the substrate for each application will vary depending on the type of surfactant selected and the component polymers used. In general, the surfactant may be added, topically or internally, in the range of from about 0.1 to about 5%, preferably from about 0.3% to about 4%, by weight of the substrate or the fibers of the substrate.

Increasing Viscosity

Another method of substantially maintaining the chemical component on the surface of the substrate is by increasing the viscosity before application onto the substrate. This prevents the saturation of the substrate with the chemical component. Generally there are two methods for increasing the viscosity of the chemical component: (i) application onto the substrate at the transition temperature of the chemical component; and (ii) introducing a thickener to the chemical component mixture before application onto the substrate. A combination of these methods is preferable.

Phase Transition Temperature Application to the Substrate

One method of maintaining the chemical component on the surface of the substrate is to apply the chemical component to the substrate at the phase transition temperature of the chemical component. This method can be employed with any chemical component wherein the phase transition temperature of the chemical component is above about 35° C. (e.g., viscous at room temperature). Phase transition temperature is defined, as used herein, as the temperature at which the chemical component transforms from a fluid, liquid state to a viscous state. In essence, this method applies the chemical component at the temperature at which the chemical component becomes viscous from a fluid liquid state during the cooling process.

Typically, the chemical component is applied onto the substrate by melting or heating. Alternatively, the chemical component can be heated and dissolved into a solvent before application to the substrate. However, some chemical components may be viscous yet fluid enough to be applied without heating. If a chemical component has a transition temperature at about room temperature or slightly above room temperature the other methods within this section must be employed to maintain the chemical component on the surface of the substrate. The transition temperatures (also known as melting point) of most chemicals may be easily obtained from the *Merck Index*, Tenth Edition (1983) and the *CTFA Cosmetic Ingredient Handbook*, Second Edition, (1992), which are incorporated by reference herein in their entirety.

A corollary to transition temperature application to the substrate is supercooling the chemical component upon application to the substrate. By supercooling is meant that the cooling rate is artificially increase above the normal ambient temperature cooling rate. This provides the dual benefit of having fluidity of the chemical component during processing yet reaching the phase transition temperature before the substrate is saturated by the chemical component. This method would be used when a chemical component is viscous and plastic at room temperature.

Thickening Agent:

If the chemical component is a liquid at room temperature (e.g., not viscous), the chemical component will not remain primarily on the surface of the substrate. Instead, the chemical component will tend to migrate and flow into the void volume of the substrate. The present method provides a solution by introducing a thickening agent into the chemical component. This increases the viscosity of the chemical component thereby achieving an equivalent result as phase transition temperature application to the substrate. Because the viscosity of the chemical component is effectively increased, it remains substantially on the surface of the substrate without saturating the substrate. Generally, the thickening agent must be viscous at room temperature, and it must be miscible in the chemical component. Phase transition temperatures and suitable viscosities of thickening agent will vary drastically upon the particular thickener. However, typically, the phase transition temperature of the thickening agent must be greater than about 35° C., preferably greater than about 40° C.

Generally, anything that is viscous at room temperature can be a thickener. The *CTFA Cosmetic Ingredient Handbook*, Second Edition, (1992), which is incorporated by reference herein in its entirety, discloses many appropriate thickeners. In fact, any conditioning agent, disclosed above, that is more viscous than the chemical component and is miscible in the chemical component can be an appropriate thickener.

Nonlimiting examples of useful thickening agents of the present invention are selected from the group consisting of fatty alcohols, fatty acids, fatty alcohol ethoxylates having an average degree of ethoxylation ranging from 2 to about 30, sorbitan esters, glyceryl esters, polyglyceryl esters, methyl glucose esters, sucrose esters, sorbitan ester ethoxylates, natural and synthetic waxes, polyacrylic and hydrophobically modified polyacrylic resins, starches, gums, cellulose ethers, polycationic polymers, nonionic polymers, polyethylene glycols (PEG), and mixtures thereof.

Nonlimiting examples of useful thickening agents in the present invention include stearic acid, behenic acid, stearyl alcohol, cetyl alcohol, sorbitan monooleate, sorbitan sesquioleate, sorbitan monoisostearate, sorbitan stearates, sorbitan trioolate, sorbitan tristearate, sorbitan dipalmitates, sorbitan isostearate, glyceryl oleate, glyceryl monostearate, glyceryl monopalmitate, glyceryl monobehenate, polyglyceryl-4 isostearate, polyglyceryl-3 oleate, diglycerol monooleate, tetraglycerol monooleate, methyl glucose dioleate, methyl glucose sesquiisostearate, sucrose stearate, sucrose trilaurate, sucrose distearate oleth-2, oleth-3, steareth-2, PEG-40 sorbitan peroleate, Polysorbate-80, beeswax, polyethylene wax, CARBOPOL, PEMULEN, corn starch, potato starch, tapioca, guar gum, gum arabic, hydroxypropyl cellulose, hydroxyethyl cellulose, carboxymethyl cellulose, RETEN 201, KYMENE 557H®, ACCO 7112, CARBOWAX.

Nonuniform Application to the Substrate

Another method of substantially maintaining the chemical component on the surface of the substrate is by applying the chemical component nonuniformly to the surface of the substrate. By "nonuniform" is meant that the amount, pattern of distribution, etc. of the chemical component can vary over the surface of the substrate. For example, some portions of the surface of the substrate can have greater or lesser amounts of the chemical component, including portions of the surface that do not have any chemical component.

Order of Application of Ingredients to the Substrate

Another method of substantially maintaining the chemical component on the surface of the substrate is by determining the order of application of ingredients to the substrate. Generally, the best results are obtained when the chemical component is added onto a dry substrate. Thus, applying the lathering surfactant first, and then drying the surfactant treated substrate before application of the chemical component will greatly enhance the delivery of the chemical component.

METHODS OF CLEANSING AND TREATING THE SKIN OR HAIR

The present invention also relates to a method of cleansing and treating the skin or hair with a personal cleansing article of the present invention. These methods comprise the steps of wetting with water a substantially dry, disposable, single use personal cleansing article comprising a water insoluble substrate, a lathering surfactant, and a skin care active component, and contacting the skin or hair with such wetted article. In further embodiments, the present invention is also useful for delivering various conditioning agents to the skin or hair.

The articles of the present invention are substantially dry and are intended to be wetted with water prior to use. The article is wetted by immersion in water or by placing it under a stream of water. Lather is generated from the article by mechanically agitating and/or deforming the article either prior to or during contact of the article with the skin or hair. The resulting lather is useful for cleansing and treating the skin or hair. During the cleansing process and subsequent rinsing with water, the skin care actives and optional ingredients are deposited onto the skin or hair. Deposition of skin care actives and conditioning ingredients are enhanced by the physical contact of the substrate with the skin or hair.

METHOD OF CONSISTENTLY DEPOSITING SKIN CARE ACTIVES AND ANY CONDITIONING INGREDIENTS ONTO THE SKIN OR HAIR

The articles of the present invention are useful for consistently depositing the skin care actives of the present invention to the skin or hair. In further embodiments where a conditioning agent is present, the compositions are also useful for consistently depositing the conditioning agent to the skin or hair.

The articles of the present invention have a deposition consistency of greater than about 60%, preferably greater than about 65%, more preferably greater than about 70%, and most preferably greater than about 75%.

The deposition consistency measurement is the quotient obtained from dividing the deposition of skin care actives via "non-ideal lathering and use" by deposition of skin care actives via "ideal lathering and use." Non-ideal lathering, as used herein, means that lathering is achieved by rubbing the surface of the article containing the skin care actives and then contacting the skin or hair with the same surface. This causes inefficient deposition of the skin care actives because some of the skin care actives become emulsified by the surfactant. Ideal lathering, as used herein, means that lathering is achieved by rubbing the surface of the article not containing skin care actives and then contacting the skin or hair with the surface containing the skin care actives. The same reference points would apply if both surfaces of the substrate are treated with the skin care actives (e.g. deposition obtained from lathering and contacting the skin with the same lathered surface containing emulsified skin care actives versus contacting the skin with the non-lathered surface which contains non-emulsified skin care actives). Deposition consistency is maximized when the hardness value of the skin care active component is greater than about 0.02 kg.

Quantification of the skin care actives deposited on the skin or hair can be measured using a variety of standard analytical techniques well known to the chemist of ordinary skill in the art. Such methods include for instance extraction of an area of the skin or hair with a suitable solvent followed by analysis by chromatography (i.e. gas chromatography, liquid chromatography, supercritical fluid chromatography, etc.), IR spectroscopy, UV/VIS spectroscopy, mass spectrometry, etc. Direct measurements can also be made on the skin or hair by techniques such as IR spectroscopy, UV/VIS spectroscopy, opacity measurements, fluoresce spectroscopy, ESCA spectroscopy, and the like.

In a typical method for measuring deposition, a article of the present invention is wetted with water and squeezed and agitated to generate a lather. The article is then rubbed for approximately 15 seconds on a site, approximately about 25 cm$^2$ to about 300 cm$^2$, preferably about 50 cm$^2$ to about 100 cm$^2$, on the skin or head which has been demarcated using an appropriate indelible marker. The site is then rinsed for approximately 10 seconds and then allowed to air dry for approximately 10 minutes. The site is then either extracted and the extracts analyzed, or analyzed directly using any techniques such as those exemplified above.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name, and all weights are in percent actives. The substrate used in all examples is a carded, hydroentangled non-woven material comprising 70% rayon and 30% polyester. It is marketed as Chicopee C5763 by the Chicopee Division of Polymer Group, Inc. This substrate has a basis weight of about 70 grams per square meter and contains apertures of about 2 mm in diameter, spaced at a frequency of about 8 apertures per linear inch.

Examples (1–5)

I. The Surfactant Phase

In a suitable vessel, the following ingredients are mixed at room temperature. Apply heat if necessary to disperse completely.

| Ingredients | Weight Percent | | | | |
| --- | --- | --- | --- | --- | --- |
| | Example 1 | Example 2 | Example 3 | Example 4 | Example 5 |
| Water | QS 100 | QS 100 | QS 100 | QS 100 | QS 100 |
| Polyquaternium-10 | 0.25 | — | — | — | — |
| PEG 14M | 0.5 | — | — | 0.5 | — |
| Hydroxypropyltrimonium Chloride | — | — | — | — | 0.5 |
| Hydroxyelthylcellulose | — | 0.25 | — | — | — |
| Guar Gum | — | 0.25 | — | — | — |

While the above mixture is being mixed the following ingredients are added to the mixture.

| | | | | | |
| --- | --- | --- | --- | --- | --- |
| Disodium EDTA | 0.10 | 0.10 | 0.10 | 0.10 | 0.10 |
| Sodium Lauroyl Sarcosinate | 3.33 | 3.33 | 3.33 | 3.33 | 3.33 |
| Sodium Lauroamphoacetate | — | — | — | — | 3.33 |
| Cocamidopropyl Betaine | 3.33 | 3.33 | 3.33 | 3.33 | — |
| Decyl Polyglucoside | 3.33 | 3.33 | 3.33 | 3.33 | 3.33 |
| Methyl Paraben | 0.25 | 0.25 | 0.25 | 0.25 | 0.25 |
| Phenoxyethanol | 0.3 | 0.3 | 0.3 | 0.3 | 0.3 |
| Benzyl Alcohol | 0.3 | 0.3 | 0.3 | 0.3 | 0.3 |

In a separate mixing vessel add the following. Mix (with heat to 40° C. if necessary) until propyl paraben is dissolved.

| | | | | | |
| --- | --- | --- | --- | --- | --- |
| Water | 2.0 | 2.0 | 2.0 | 2.0 | 2.0 |
| Butylene Glycol | 2.0 | 2.0 | 2.0 | 2.0 | 2.0 |
| Propyl Paraben | 0.15 | 0.15 | 0.15 | 0.15 | 0.15 |

Add this mixture to the first mixing vessel. Apply 1.5–2.5 g of the resultant mixture to the substrate, as described herein, and then dry.

II. The Skin Care Active phase

In a suitable vessel, the following ingredients are mixed at room temperature. Apply heat if necessary to disperse completely.

| | | | | | |
|---|---|---|---|---|---|
| Water | QS 100 | QS 100 | QS 100 | QS 100 | QS 100 |
| Glycerin | 60.0 | 40.0 | 0.0 | 50.0 | 30.0 |
| Dex Panthenol | 1.0 | 4.0 | 2.0 | 4.0 | 4.0 |
| Urea | — | — | — | 2.0 | — |
| PEG-30 | — | 20.0 | 25.0 | — | 5.0 |
| Lactic Acid | — | — | 4.0 | — | — |
| Dihydroxyacetone | 4.0 | — | — | — | — |
| Niacinamide | — | — | — | 5.0 | 10.0 |
| Arbutin | — | 3.0 | — | — | — |
| kojic acid | — | — | 3.0 | — | — |
| allantoin | — | — | — | 2.0 | 2.0 |
| Propylene glycol | — | 5.0 | 30.0 | — | — |
| Polyquaternium-10 | — | 3.0 | — | — | — |
| PEG 14M | 5.0 | 3.0 | 3.0 | 3.0 | 5.0 |
| Hydroxyethylcellulose | — | — | 2.0 | 2.0 | — |
| Guar Gum | — | — | — | 1.0 | — |

Apply 0.10 to 1.0 grams of this phase to the dry substrate already containing the materials from the Surfactant Phase. Allow any added water to dry. The resulting cleansing article is used by wetting with water and is useful for cleansing the skin or hair and for depositing the skin care active component onto the skin or hair. Alternatively, the Skin Care Active Phase can be added onto or impregnated into the insoluble substrate before the Surfactant Phase, as long as the surfactant is not added via dip/nip process. This alternative process is possible when using extrusion or gravure printing application methods.

Examples 6–10

I. Surfactant Phase

In a suitable vessel, the following ingredients are mixed at room temperature. Apply heat if necessary to disperse completely.

| | Weight Percent | | | | |
|---|---|---|---|---|---|
| Ingredients | Example 6 | Example 7 | Example 8 | Example 9 | Example 10 |
| Water | QS 100 | QS 100 | QS 100 | QS 100 | QS 100 |
| Polyquaternium-10 | — | — | — | 0.25 | — |
| PEG 14M | 0.5 | — | — | 0.5 | — |
| Hydroxypropyltrimonium Chloride | — | — | — | — | 0.5 |
| Hydroxyethylcellulose | — | 0.25 | — | — | — |
| Guar Gum | — | 0.25 | — | — | — |

While the above mixture is being mixed the following ingredients are added to the mixture.

| | | | | | |
|---|---|---|---|---|---|
| Disodium EDTA | 0.10 | 0.10 | 0.10 | 0.10 | 0.10 |
| Sodium Lauroyl Sarcosinate | 3.33 | 3.33 | 3.33 | 3.33 | 3.33 |
| Sodium Lauroamphoacetate | — | — | — | — | 3.33 |
| Cocamidopropyl Betaine | 3.33 | 3.33 | 3.33 | 3.33 | — |
| Decyl Polyglucoside | 3.33 | 3.33 | 3.33 | 3.33 | 3.33 |
| Methyl Paraben | 0.25 | 0.25 | 0.25 | 0.25 | 0.25 |
| Phenoxyethanol | 0.3 | 0.3 | 0.3 | 0.3 | 0.3 |
| Benzyl Alcohol | 0.3 | 0.3 | 0.3 | 0.3 | 0.3 |

In a separate mixing vessel add the following. Mix (with heat to 40° C. if necessary) until propyl paraben is dissolved.

| | | | | | |
|---|---|---|---|---|---|
| Water | 2.0 | 2.0 | 2.0 | 2.0 | 2.0 |
| Butylene Glycol | 2.0 | 2.0 | 2.0 | 2.0 | 2.0 |
| Propyl Paraben | 0.15 | 0.15 | 0.15 | 0.15 | 0.15 |

Add this mixture to the first mixing vessel. Apply 1.5–2.5 g of the resultant mixture to the substrate, as described herein, and then dry.

II: Skin Care Active Phase

In a suitable vessel, the following ingredients are mixed with heat until molten (between 75–115° C.

| | | | | | |
|---|---|---|---|---|---|
| SEFA* Cottonate | 48.00 | 43.00 | 46.00 | 48.00 | 48.00 |
| SEFA* Behenate | 12.00 | — | — | — | — |
| Petrolatum | 10.00 | 10.00 | 10.00 | 10.00 | 10.00 |
| Tribehenin | 5.00 | 5.0 | 5.0 | 5.0 | 5.0 |
| Polyethylene Wax | — | 9.0 | 9.0 | 9.0 | — |
| Paraffin | — | — | — | — | 12.00 |
| Synthetic Beeswax | — | 3.0 | 3.0 | 3.0 | — |
| C10–C30 Cholesterol/Lanosterol Esters | 18.00 | 23.00 | 23.00 | 23.00 | 20.00 |
| Vitamin E Acetate | — | 2.0 | 2.0 | 2.0 | 2.0 |

*SEFA is an acronym for sucrose esters of fatty acids

Add the following ingredients to the above molten mixture once uniform

| | | | | | |
|---|---|---|---|---|---|
| Retinyl Palmitate | — | — | 2.0 | — | 1.0 |
| PPG-15 Stearyl Ether | 5.0* | — | — | — | — |
| Salicylic Acid | 2.0* | — | — | — | — |
| Titanium Dioxide | — | 5.0 | — | — | 2.0 |

*Mix these ingredients until salicylic acid is dissolved.

Apply 0.05–0.75 grams of this phase to the substrate already containing the materials from the Surfactant phase. This Skin Care Active Phase should be applied in a liquid/molten state and then cooled. The resulting cleansing article is used by wetting with water and is useful for cleansing the skin or hair and for depositing the skin care active component onto the skin or hair in a consistent manner. Alternatively, the Skin Care Active Phase can be added onto or impregnated into the insoluble substrate before the Surfactant Phase, as long as the surfactant is not added via dip/nip process. This alternative process is possible when using extrusion or gravure printing application methods.

Examples 11–15

I. Surfactant Phase

In a suitable vessel, the following ingredients are mixed at room temperature. Apply heat if necessary to disperse completely.

| | Weight Percent | | | | |
|---|---|---|---|---|---|
| Ingredients | Example 1 | Example 2 | Example 3 | Example 4 | Example 5 |
| Water | QS 100 | QS 100 | QS 100 | QS 100 | QS 100 |
| Polyquaternium-10 | 0.25 | — | — | — | — |
| PEG 14M | 0.5 | — | — | 0.5 | — |
| Hydroxypropyltrimonium | — | — | — | — | 0.5 |

-continued

| Ingredients | Example 1 | Example 2 | Example 3 | Example 4 | Example 5 |
|---|---|---|---|---|---|
| Chloride | | | | | |
| Hydroxyethylcellulose | — | 0.25 | — | — | — |
| Guar Gum | — | 0.25 | — | — | — |

While the above mixture is being mixed the following ingredients are added to the mixture.

| | | | | | |
|---|---|---|---|---|---|
| Disodium EDTA | 0.10 | 0.10 | 0.10 | 0.10 | 0.10 |
| Sodium Lauroyl Sarcosinate | 3.33 | 3.33 | 3.33 | 3.33 | 3.33 |
| Sodium Lauroamphoacetate | — | — | — | — | 3.33 |
| Cocamidopropyl Betaine | 3.33 | 3.33 | 3.33 | 3.33 | — |
| Decyl Polyglucoside | 3.33 | 3.33 | 3.33 | 3.33 | 3.33 |
| Methyl Paraben | 0.25 | 0.25 | 0.25 | 0.25 | 0.25 |
| Phenoxyethanol | 0.3 | 0.3 | 0.3 | 0.3 | 0.3 |
| Benzyl Alcohol | 0.3 | 0.3 | 0.3 | 0.3 | 0.3 |

In a separate mixing vessel add the following. Mix (with heat to 40° C. if necessary) until the propyl paraben is dissolved.

| | | | | | |
|---|---|---|---|---|---|
| Water | 2.0 | 2.0 | 2.0 | 2.0 | 2.0 |
| Butylene Glycol | 2.0 | 2.0 | 2.0 | 2.0 | 2.0 |
| Propyl Paraben | 0.15 | 0.15 | 0.15 | 0.15 | 0.15 |

Add this mixture to the first mixing vessel. Apply 1.5–2.5 g of the resultant mixture to the substrate, as described herein, and then dry.

II. The Skin Care Emulsion Phase

In a suitable vessel, the following ingredients are mixed at with heat until uniform (75–115° C.).

| | | | | | |
|---|---|---|---|---|---|
| SEFA* Cottonate | 27.36 | 25.36 | 46.00 | 48.00 | 48.00 |
| SEFA* Behenate | — | — | — | — | — |
| Petrolatum | 5.7 | 5.7 | 10.00 | 10.00 | 10.00 |
| Tribehenin | 2.85 | 2.85 | 5.0 | 5.0 | 5.0 |
| Polyethylene Wax | 5.13 | 5.13 | 9.0 | 9.0 | — |
| Paraffin | — | — | — | — | 12.00 |
| Synthetic Beeswax | 1.71 | 1.71 | 3.0 | 3.0 | — |
| C10–C30 Cholesterol/Lanosterol Esters | 13.1 | 13.1 | 23.00 | 23.00 | 20.00 |
| Vitamin E Acetate | 1.15 | 1.15 | 2.0 | 2.0 | 2.0 |
| Decaglyceryl Dipalmitate | 0.3 | — | 0.3 | 0.3 | — |
| Triglyceryl Monostearate | 2.7 | 0.3 | 2.7 | 2.7 | 0.3 |
| Decaglyceryl Stearate | — | 2.7 | — | — | 2.7 |
| Polyglyceryl Tristearate | — | — | — | — | — |
| Retinyl Palmitate | — | 2.0 | 2.0 | — | 1.0 |

Mix the following ingredients at room temperature. Add slowly with agitation to the above mixture once it is uniform.

| | | | | | |
|---|---|---|---|---|---|
| Water | 5.0 | 2.0 | 11.0 | 10.0 | 0.0 |
| Glycerin | 30.0 | 9.0 | 5.0 | 5.0 | 10.0 |
| Dex Panthenol | 1.0 | 1.0 | 2.0 | 4.0 | 3.0 |

-continued

| | | | | | |
|---|---|---|---|---|---|
| Urea | — | — | — | 2.0 | — |
| PEG-30 | — | 20.0 | 15.0 | 12.0 | 10.0 |
| Lactic Acid | — | — | 4.0 | — | — |
| Dihydroxyacetone | 4.0 | — | — | — | — |
| Niacinamide | — | — | — | 5.0 | 10.0 |
| Arbutin | — | 3.0 | — | — | — |
| kojic acid | — | — | 3.0 | — | — |
| allantoin | — | — | — | 2.0 | — |
| Propylene glycol | — | 5.0 | — | — | 7.0 |

Apply 0.05–1.5 grams of this phase to the dry substrate already containing the materials from the Surfactant Phase and allow to cool. The resulting cleansing article is used by wetting with water and is useful for cleansing the skin or hair and for depositing the skin care active component onto the skin or hair. Alternatively, the Skin Care Emulsion Phase can be added onto or impregnated into the insoluble substrate before the Surfactant Phase, as long as the surfactant is not added via dip/nip process. This alternative process is possible when using extrusion or gravure printing application methods.

The following alternative manufacturing procedures can be applied to any of the examples described hereinbefore. For treating a substrate having two layers, the lathering surfactants, skin care active component, and optional ingredients are separately or simultaneously added onto or impregnated into either surface of (i) either or both layers prior to combining the layers into a laminate, or (ii) after the layers are combined into a laminate. The process of adding onto or impregnating into the substrate the surfactant and/or conditioning component is achieved by spraying, printing, splashing, dipping, or coating.

Similarly, the lathering surfactant and the skin care active component can be added to the substrate in any order. Nonlimiting examples of the process sequences include (i) first adding surfactant to the second layer, then joining the substrate, then treating with the skin care active component; (ii) first combining surfactant with skin care active component then treating the second layer, then joining the two layers; (iii) prior to joining the two layers, treating the second layer with the surfactant first and then the skin care active component second, then joining the two layers.

In alternative embodiments, other substrates such as woven substrates, hydroentangled substrates, natural sponges, synthetic sponges, or polymeric netted meshes are substituted for the present substrate.

What is claimed is:

1. A disposable, single use personal care cleansing article comprising:
   (A) a water insoluble substrate,
   (B) from about 0.5% to about 40%, by weight of said insoluble substrate, of at least one lathering surfactant added onto or impregnated into said substrate, and
   (C) from about 0.001% to about 50%, by weight of said insoluble substrate, of a skin care active component comprising at least one skin care active selected from the group consisting of anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; and mixtures thereof, which skin care active component is added onto or impregnated into said substrate,
wherein said article is substantially dry, and wherein said article is capable of generating an Average Lather Volume of greater than or equal to about 30 ml.

2. An article according to claim 1 wherein said cleansing article deposits greater than about 0.001 $\mu g/cm^2$ of said skin care active to the surface of the skin or hair.

3. An article according to claim 1 further comprising at least one deposition aid onto or impregnated into the substrate.

4. An article according to claim 1 wherein said skin care active component comprises materials selected from the group consisting of water soluble skin care agents, oil soluble skin care agents, skin care emulsions, and mixtures thereof.

5. An article according to claim 1 wherein said active ingredient is selected from the group consisting of salicylic acid, niacinamide, nicotinic acid, benzoyl peroxide, cis-retinoic acid, trans-retinoic acid, retinol, retinyl palmitate, phytic acid, N-acetyl L-cysteine, azelaic acid, lipoic acid, resorcinol, lactic acid, glycolic acid, ibuprofen, naproxen, hydrocortisone, phenoxyethanol, phenoxypropanol, phenoxyisopropanol, 2,4,4,'-trichloro-2'-hydroxy diphenyl ether, 3,4,4'-trichlorocarbanilide, 2-ethylhexyl p-methoxycinnamic acid, oxybenzone, 2-phenylbenzimidozole-5-sulfonic acid, dihydroxyacetone, panthenol, arbutin, deoxyarbutin, kojic acid, aflantoin, cholesterol, C10–C30 cholesterol/lanosterol esters, tocopherol, tocopheryl acetate, and mixtures thereof.

6. An article according to claim 4 wherein said skin care active emulsion comprises,
  (A) a discontinuous phase comprising water soluble compounds selected from the group consisting of water, water soluble skin care actives, and mixtures thereof; and
  (B) a continuous phase comprising oil soluble skin care actives.

7. An article according to claim 6 further comprising from 0% to about 20% by weight of said skin care active emulsion of an emulsifier capable of forming an emulsion of said discontinuous and continuous phases, wherein said emulsifier is selected from one or more emulsifiers such that the weighted arithmetic mean HLB value is from about 1 to about 7.

8. An article according to claim 2 wherein said deposition aid is selected from the group consisting of nonionic polymers, cationic polymers, non-polymeric cationic surfactants, and mixtures thereof.

9. An article according to claim 8 wherein said deposition aid is selected from the group consisting of gums, cellulose derived polymers, protein derived polymers, polymeric ethers, synthetic polymers, and mixtures thereof.

10. An article according to claim 1 wherein said water Insoluble substrate comprises one or more materials selected from the group consisting of silks; keratins; celuloses, acetates, acrylics, cellulose esters, modacrylics, polyamides, polyolefins, polyvinyl alcohols, wood pulp, cotton, hemp, jute, flax, acrylics, nylons, polyesters, polyproylenes, polyethylenes, polyvinyl acetates, polyurethanes, rayon, and mixtures thereof.

11. An article according to claim 10 wherein said water insoluble substrate is selected from the group consisting of nonwoven substrates, woven substrates, hydroentangled substrates, natural sponges, synthetic sponges, polymeric netted meshes, formed films, and mixtures thereof.

12. An article according to claim 11 wherein said water insoluble substrate comprises a nonwoven sheet of fibers selected from the group consisting of rayon fibers, cellulose fibers, polyester fibers, and mixtures thereof.

13. An article according to claim 11 wherein said water insoluble substrate comprises two or more sheets of fibers each in turn having different textures.

14. An article according to claim 1 wherein said lathering surfactant is selected from the group consisting of anionic lathering surfactants, nonionic lathering surfactants, amphoteric lathering surfactants, and mixtures thereof.

15. An article according to claim 14 wherein said anionic lathering surfactant is selected from the group consisting of sarcosinates, sulfates, isethionates, phosphates, taurates, lactylates, glutamates and mixtures thereof; wherein said nonionic lathering surfactant is selected from the group consisting of amine oxides, alkyl glucosides, alkyl polyglucosides, polyhydroxy fatty acid amides, alkoxylated fatty acid esters, sucrose esters, and mixtures thereof; and wherein said amphoteric lathering surfactant is selected from the group consisting of betaines, sultaines, hydroxysultaines, alkyliminoacetates, iminodialkanoates, aminoalkanoates, and mixtures thereof.

16. An article according to claim 1 wherein said skin care active component further comprises a conditioning component added onto or impregnated into the substrate separately from said lathering surfactant, which conditioning component comprises a conditioning agent selected from the group consisting of oil soluble conditioning agents, water soluble conditioning agents, lipid hardening materials and mixtures thereof.

17. An article according to claim 6 wherein said discontinuous phase further comprises a water soluble conditioning agent and wherein said continuous phase further comprises a conditioning agent selected from the group consisting of oil soluble conditioning agents, lipid hardening materials, and mixtures thereof.

18. An article according to claim 16 wherein said skin care active component has a hardness value of greater than about 0.02 kg.

19. An article according to claim 16 wherein said oil soluble conditioning agent and said lipid hardening material are selected from the group consisting of fatty acids, esters of fatty acids, fatty alcohols, ethoxylated alcohols, polyol polyesters, glycerin mono-esters, glycerin polyesters, epidermal and sebaceous hydrocarbons, lanolin, mineral oil, silicone oil, silicone gum, vegetable oil, vegetable oil adduct, petrolatum, nonionic polymers, hydrogenated vegetable oils, nonionic polymers, natural waxes, synthetic waxes, polyolefinic glycols, polyolefinic monoester, polyolefinic polyesters, cholesterols, cholesterol esters, and mixtures thereof; and wherein said water soluble conditioning agent is selected from the group consisting of glycerin, glycerol, propylene glycol, polypropylene glycols, polyethylene glycols, ethyl hexanediol, hexylene glycols, other aliphatic alcohols, panthenol, urea, cationic polymers, polyols, glycolic acid, lactic acid, and mixtures thereof.

20. A method of manufacturing a disposable, single use personal cleansing article comprising the steps of
  (A) separately or simultaneously adding onto or impregnating into a water insoluble substrate,
    (i) from about 0.5% to about 40%, by weight of said insoluble substrate, of at least one lathering surfactant added onto or impregnated into said substrate, and
    (ii) from about 0.001% to about 50%, by weight of said insoluble substrate, of a skin care active component comprising at least one skin care active selected from the group consisting of water soluble skin care actives, oil soluble skin care actives and mixtures thereof, and (B) substantially drying the treated article in Step (A), wherein the resulting article is capable of generating an Average Lather Volume of greater than or equal to about 30 ml.

21. A method of manufacture according to claim 20 wherein said skin care active component is added onto or impregnated into said water insoluble substrate separately from said lathering surfactant in Step (A).

22. A method of manufacture according to claim 21 wherein Step (A) further comprises a compound selected from the group consisting of deposition aids, oil soluble conditioning agents, water soluble conditioning agents, lipid hardening materials, and mixtures thereof.

23. A method of cleansing the skin or hair and depositing a skin care active onto the skin or hair with a personal cleansing article, comprising the steps of:
(A) generating an Average Lather Volume of greater than or equal to about 30 ml. by wetting with water and agitating a substantially dry, disposable, single use personal cleansing article comprising:
   (i) a water insoluble substrate,
   (ii) from about 0.5% to about 40%, by weight of said insoluble substrate, of at least one lathering surfactant, and
   (iii) from about 0.001% to about 50%, by weight of said insoluble substrate, of a skin care active component comprising at least one skin care active selected from the group consisting of water soluble skin care actives, oil soluble skin care actives and mixtures thereof, and
(B) contacting the skin or hair with said lathered article.

24. A method according to claim 23 wherein said article of Step (A) further comprises a compound selected from the group consisting of deposition aids, oil soluble conditioning agents, water soluble conditioning agents, lipid hardening materials, and a mixtures thereof.

25. A method of depositing greater than about 0.001 $\mu g/cm^2$ of said skin care active to the surface of the skin or hair, such method comprising the steps of
(A) generating lather by wetting said article according to claim 1, and
(B) contacting the skin or hair with said lathered article.

26. A method according to claim 25 wherein said article further comprises a compound selected from the group consisting of deposition aids, oil soluble conditioning agents, water soluble conditioning agents, lipid hardening materials, and mixtures thereof.

27. A method according to claim 25 wherein said skin care actives are delivered to the skin or hair with a deposition consistency of at least about 60%.

28. A method according to claim 27 wherein said article further comprises a compound selected from the group consisting of deposition aids, oil soluble conditioning agents, water soluble conditioning agents, lipid hardening materials, and a mixtures thereof.

29. An article according to claim 1, wherein the skin care active is selected from tocopherol, tocopheryl acetate, panthenol, C10–C30 cholesterol/lanosterol esters, and mixtures thereof and the lathering surfactant is an anionic lathering surfactant.

* * * * *